US012068069B1

(12) United States Patent
Perry et al.

(10) Patent No.: US 12,068,069 B1
(45) Date of Patent: *Aug. 20, 2024

(54) SYSTEMS AND METHODS FOR PROCESSING REAL-TIME AND HISTORICAL DATA AND GENERATING NURSING UNIT HEALTH SCORES

(71) Applicant: TeleTracking Technologies, Inc., Pittsburgh, PA (US)

(72) Inventors: Thomas Perry, Pittsburgh, PA (US); Joseph C. Schuck, Pittsburgh, PA (US)

(73) Assignee: TELETRACKING TECHNOLOGIES, INC., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/825,691

(22) Filed: May 26, 2022

Related U.S. Application Data

(63) Continuation of application No. 16/034,024, filed on Jul. 12, 2018, now Pat. No. 11,348,679.

(Continued)

(51) Int. Cl.
    *G16H 40/20* (2018.01)
    *G06F 3/0484* (2022.01)
    *G06Q 10/0639* (2023.01)

(52) U.S. Cl.
    CPC ........... *G16H 40/20* (2018.01); *G06F 3/0484* (2013.01); *G06Q 10/06393* (2013.01)

(58) Field of Classification Search
    CPC . G16H 40/20; G06F 3/0484; G06Q 10/06393

(Continued)

(56) References Cited

U.S. PATENT DOCUMENTS 8,738,487 B1 5/2014 Shmidt et al.
2002/0107769 A1* 8/2002 Dashefsky ............. G06Q 40/03
                                                              705/35

(Continued)

FOREIGN PATENT DOCUMENTS

WO    2015157570 A2    10/2015
WO    2015157573 A2    10/2015

(Continued)

OTHER PUBLICATIONS

Done, Nicolae; The Effects of Global Budget Payments on Hospital Utilization and Quality in Rural Maryland; The Johns Hopkins University. ProQuest Dissertations Publishing, 2017. 27606852. (Year: 2017).*

*Primary Examiner* — Hiep V Nguyen
(74) *Attorney, Agent, or Firm* — FERENCE & ASSOCIATES LLC

(57) ABSTRACT

One embodiment provides a method including receiving current census data for departments of a hospital. The method includes projecting future census data for the departments. The method includes displaying, in a dynamic user interface on a facility utilization visualization application, a graphical view of a current utilization of the departments of the hospital determined from the current census data and a projected utilization of the departments determined from the future census data. The method includes dynamically updating the dynamic user interface in real-time based upon at least one of receipt of new real-time data, receipt of new historical data, and a new analysis of the real-time and the historical data. Other aspects are described and claimed.

20 Claims, 15 Drawing Sheets

Related U.S. Application Data

(60) Provisional application No. 62/531,852, filed on Jul. 12, 2017.

(58) Field of Classification Search
USPC .............................................................. 705/2
See application file for complete search history.

(56) References Cited

U.S. PATENT DOCUMENTS

| | | |
|---|---|---|
| 2003/0050794 A1 | 3/2003 | Keck |
| 2003/0074222 A1 | 4/2003 | Rosow et al. |
| 2003/0158749 A1* | 8/2003 | Olchanski .............. G16H 70/20 |
| | | 705/2 |
| 2007/0083391 A1 | 4/2007 | Gorup et al. |
| 2013/0173355 A1 | 7/2013 | Barcenas |
| 2014/0136458 A1* | 5/2014 | Levin ..................... G16H 50/20 |
| | | 706/21 |
| 2015/0213225 A1 | 7/2015 | Amarasingham et al. |

FOREIGN PATENT DOCUMENTS

| | | | | |
|---|---|---|---|---|
| WO | WO-2015157570 A1 * | 10/2015 | ............. | G06Q 10/06 |
| WO | WO-2015157573 A2 * | 10/2015 | ............. | G06Q 10/06 |

* cited by examiner

SYSTEMS AND METHODS FOR PROCESSING REAL-TIME AND HISTORICAL DATA AND GENERATING NURSING UNIT HEALTH SCORES

CROSS REFERENCE TO RELATED APPLICATIONS

This application claims priority to co-pending U.S. patent application Ser. No. 16/034,024, filed Jul. 12, 2018, titled "Systems and Methods for Processing Real-Time and Historical Data and Generating Nursing Unit Health Scores," which claims priority from U.S. Provisional Application Ser. No. 62/531,852, filed Jul. 12, 2017, the contents of both of which are incorporated by reference herein.

TECHNICAL FIELD

The present disclosure is directed to the technical field of data processing and graphical user interface generation. More particularly, disclosed embodiments are directed to aggregating and analyzing real time and historical data collected from one or more networked sources to generate graphical user interfaces for providing simplified indications of performance efficiency.

BACKGROUND

Modern health care facilities have highly skilled personnel, high-tech patient monitoring systems, employee communication systems, and in some instances, patient and equipment location tracking systems. High efficiency, however, still evades many modern facilities, and many hospitals still fail to deliver the best possible health care to their patients, and fail to operate at maximum possible capacity. There are multiple underlying reasons for inefficiencies.

As such, supervisors and/or centralized staffing coordinators do not have adequate data available regarding upcoming staffing needs and staffing optimization, and are left to guess what level of staffing might be adequate. As a result, caregivers and hospital personnel may arrive at inappropriate times or cause bottlenecks in certain departments by bringing too many patients at the same time. Such inefficiencies decrease the quality of care to all admitted patients, as well as preventing the hospital from discharging patients quickly to admit more new patients. While vast amounts of real-time and historical data may be available in some hospitals, existing hospitals lack the ability to synthesize and display these large amounts of information quickly and in a way that is easy-to-read for hospital personnel.

In view of the problems facing hospitals and other health care facilities, improved systems and methods for understanding facility utilization are needed.

BRIEF SUMMARY

In summary, one aspect provides a method, the method including: receiving current census data for departments of a hospital, wherein the current census data comprises real-time data identifying a number of patients currently admitted within a given of the departments and a current status of the patients; projecting future census data for the departments, wherein the projecting comprises identifying a performance benchmark for a given of the departments by analyzing real-time data and historical data corresponding to the real-time data, wherein the performance benchmark is based upon at least one quality measurement metric; displaying, in a dynamic user interface on a facility utilization visualization application, a graphical view of a current utilization of the departments of the hospital determined from the current census data and a projected utilization of the departments determined from the future census data; and dynamically updating the dynamic user interface in real-time based upon at least one of receipt of new real-time data, receipt of new historical data, and a new analysis of the real-time and the historical data.

Another aspect provides an information handling device, the information handling device including: a processor; a memory device that stores instructions that, when executed by the processor, causes the information handling device to: receive current census data for departments of a hospital, wherein the current census data comprises real-time data identifying a number of patients currently admitted within a given of the departments and a current status of the patients; project future census data for the departments, wherein the projecting comprises identifying a performance benchmark for a given of the departments by analyzing real-time data and historical data corresponding to the real-time data, wherein the performance benchmark is based upon at least one quality measurement metric; display, in a dynamic user interface on a facility utilization visualization application, a graphical view of a current utilization of the departments of the hospital determined from the current census data and a projected utilization of the departments determined from the future census data; and dynamically update the dynamic user interface in real-time based upon at least one of receipt of new real-time data, receipt of new historical data, and a new analysis of the real-time and the historical data.

A further aspect provides a product, the product including: a computer-readable storage device that stores executable code that, when executed by a processor, causes the product to: receive current census data for departments of a hospital, wherein the current census data comprises real-time data identifying a number of patients currently admitted within a given of the departments and a current status of the patients; project future census data for the departments, wherein the projecting comprises identifying a performance benchmark for a given of the departments by analyzing real-time data and historical data corresponding to the real-time data, wherein the performance benchmark is based upon at least one quality measurement metric; display, in a dynamic user interface on a facility utilization visualization application, a graphical view of a current utilization of the departments of the hospital determined from the current census data and a projected utilization of the departments determined from the future census data; and dynamically update the dynamic user interface in real-time based upon at least one of receipt of new real-time data, receipt of new historical data, and a new analysis of the real-time and the historical data.

The foregoing general description and the following detailed description are exemplary and explanatory only and are not restrictive of the claims.

BRIEF DESCRIPTION OF THE SEVERAL VIEWS OF THE DRAWINGS

The accompanying drawings, which are incorporated in and constitute a part of this specification, illustrate several embodiments and, together with the description, serve to explain the disclosed principles. In the drawings.

DETAILED DESCRIPTION

Reference will now be made in detail to exemplary embodiments, examples of which are illustrated in the accompanying drawings and disclosed herein. Wherever convenient, the same reference numbers will be used throughout the drawings to refer to the same or like parts.

Figure 1:
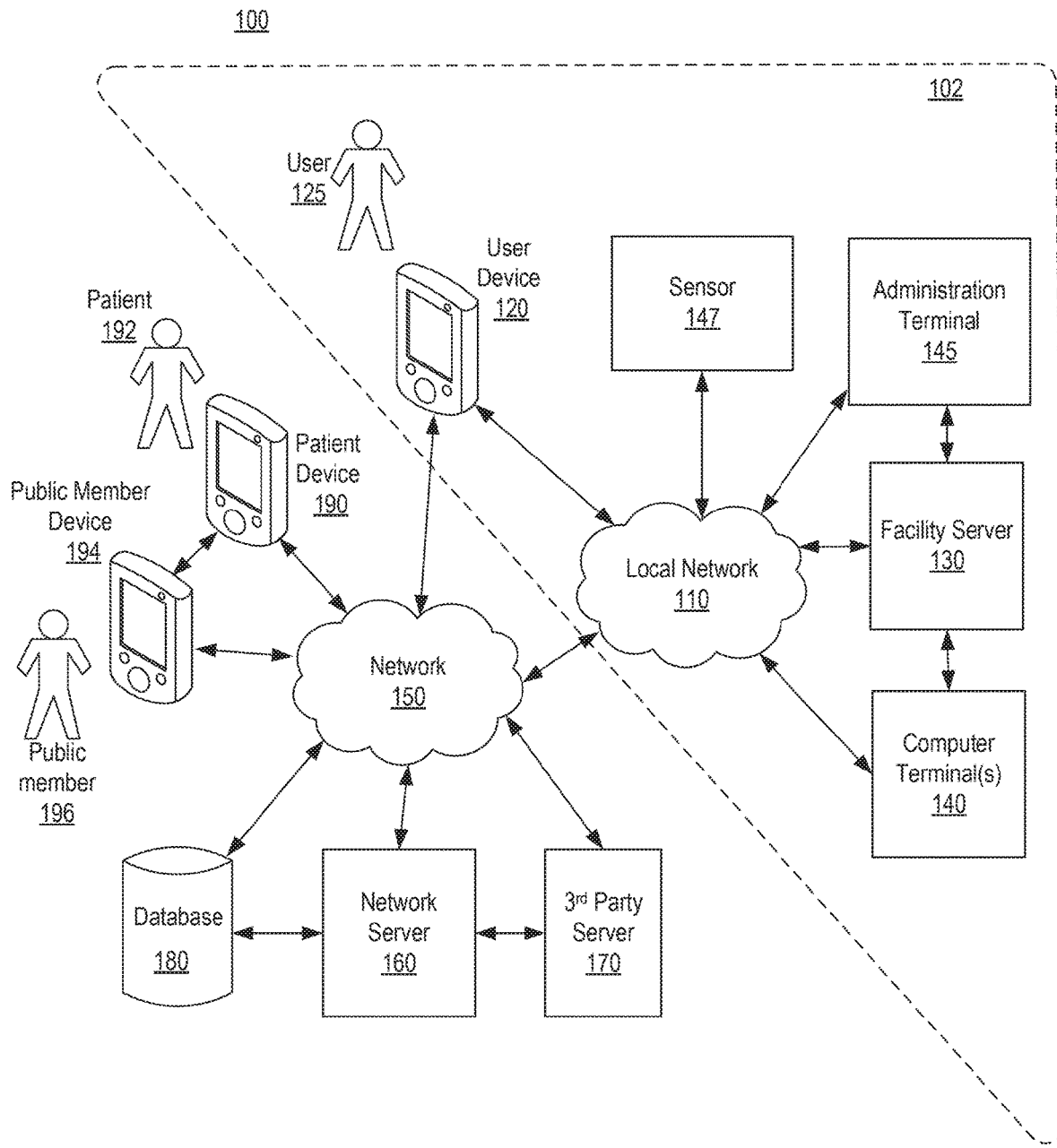
FIG. 1 depicts an example of a system environment for managing facility utilization within an organization, consistent with embodiments of the present disclosure.

FIG. 1 shows a diagram of a computer system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a medical facility such as a hospital or office building (i.e. as facility system 102) while network 150, network server 160, third party server 170, and database 180 may be external to the medical facility. Other components known to one of ordinary skill in the art may be included in system 100 to perform tasks consistent with the disclosed embodiments. For example, in some embodiments, facility system 102 may include one or more sensor devices such as sensors 147 located throughout the facility to monitor one or more conditions such as occupancy, temperature, humidity, proximity, and other parameters indicative of a status or condition of a room, area, equipment, or supplies. In some embodiments, sensors 147 may be disposed throughout one or more areas of a hospital as part of a security system or a real-time locating system. Additionally, in some embodiments sensors 147 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, touch screen monitor, or any other display. In some embodiments, computer terminal 140 may be associated with a particular room in a facility, such as a particular patient room, hotel room, conference room, or any other type of room. Thus, a message or task request received from a computer terminal 140 may automatically associate the task request or message with the room in which computer terminal 140 is installed.

Administrator terminal 145 may include a computer system or device associated with a user 125 that manages or oversees a portion of facility system 102. For example, administrator terminal 145 may comprise a computer system located at a head nurse station, a housekeeping manager's office, or any other department manager's office or station. In some embodiments, administrator terminal 145 may be a computer terminal 145 designated to a particular user or class of users, and may include any of the functions and comprise any of the hardware discussed with respect to computer terminal 145.

User 125 may be an employee in a workplace environment such as a physician, nurse, a technician, supervisor, manager, support personnel, dispatcher, or any other individual involved with the care of a patient. User 125 may operate computer terminal 140, user device 120, and/or another computer (not shown) to interact with system 100. System 100 may include multiple types of users such as, for example, caregivers, technicians, task requestors, dispatchers, and responders. Task requestors may include one or more individuals who initiate a request for a certain task to be completed, such as a nurse requesting a hospital bed. In some embodiments, dispatchers may include individuals who perform one or more tasks related to assigning requested tasks. In some embodiments, responders may include one or more individuals assigned to the requested tasks, who perform and complete the tasks.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that task assignments directed toward user 125 are sent to mobile device 120.

In some embodiments, user device 120 may communicate with facility server 130 and/or network server 160 via direct wireless communication links (not shown), or via a combination of one or more of local network 110 and/or network 150.

In some embodiments, one or more individuals such as the patient 192 or a member of the public 196 may send and receive information to facility system 102. In the example shown, patient 192 may operate patient device 190, which may be similar in form and function to user device 120. In some embodiments, patient 192 may provide information regarding location, symptoms, ratings for satisfaction of care, indication of delay, and any other information relevant to a patient diagnosis, or treatment protocol and itinerary.

Public member 196 may an individual associated with the patient who is not a hospital employee such as, for example, a primary care physician of the patient, or a relative of the patient. Public member 196 may operate public member device 194, which may be similar in form and function to devices 190 and 120.

Facility server 130 may be operated by a facility such as a hospital, business, retail location, and the like. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™, Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection. In some embodiments, local network 110 may comprise a portion of network 150 or an extension of network 150.

Network server 160, Third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with one or more third-party services such as mapping services, data analysis services, or storage services.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and interface-related functions of the disclosed embodiments.

Figure 2:
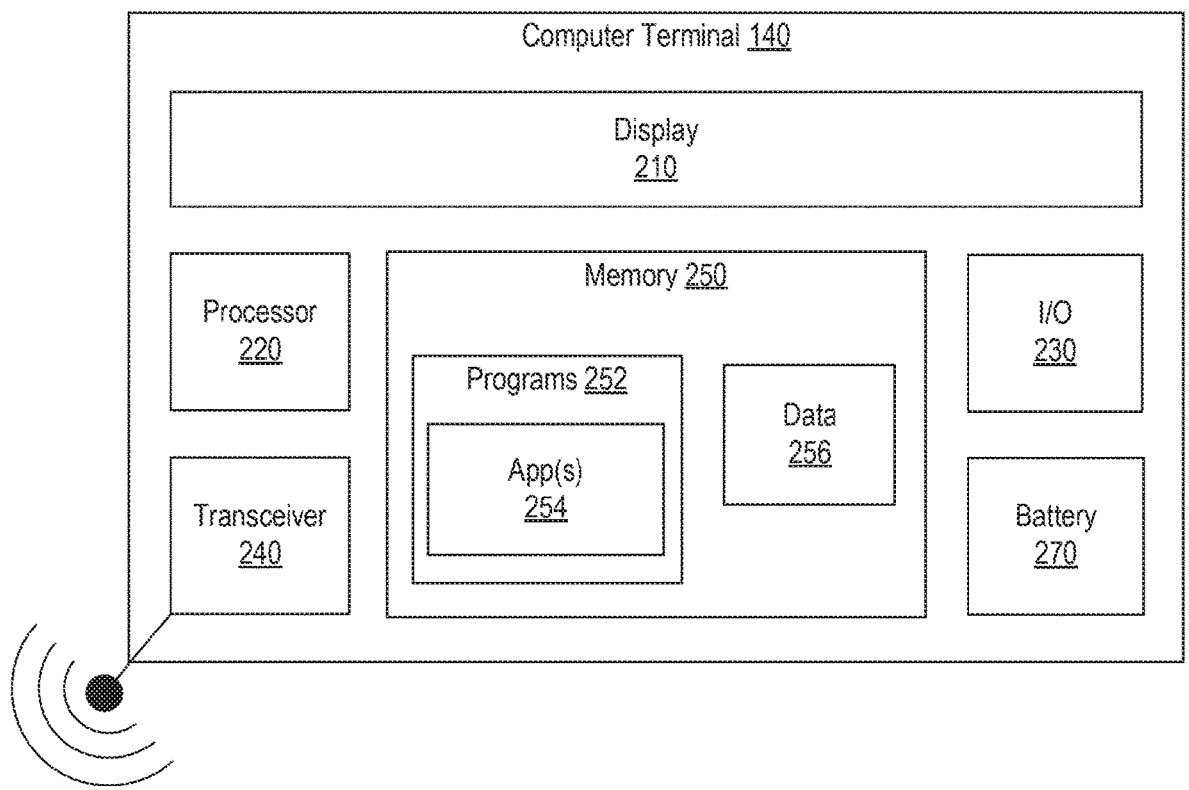
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240 memory 250, and battery 270.

Display 210 may include one or more screens for displaying task management information such as, for example, liquid crystal display (LCD), plasma, cathode ray tube (CRT), or projected screens.

Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, solid-state, tape, optical, removable, non-removable, or other type of storage device or tangible (i.e., non-transitory) computer-readable medium that stores one or more program(s) 252, such as app(s) 254, and data 256. Data 256 may include, for example, user information, patient information, facility information, and display settings and preferences.

Program(s) 252 may include operating systems (not shown) that perform known operating system functions when executed by one or more processors. By way of example, the operating systems may include Microsoft Windows™, Unix™, Linux™, Android™ and Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a facility utilization visualization app, which when executed causes computer terminal 140 to perform processes related to processing real-time and historical facility data, and generating graphical user interfaces based on the data. For example, app(s) 254 may configure computer terminal 140 to generate and display one or more dynamic facility utilization interfaces to provide users such as hospital administrators and other personnel a graphical view of the utilization of various units of an organization. The facility utilization interfaces may graphically display current and historical facility information such as available capacity of departments, or units, within a hospital, volume of transfer of patients between departments, and volume of admissions and discharges of patients to and from the hospital. Furthermore, app(s) 254 may configure computer terminal 140 to analyze the current and historical information associated with the facility to predict estimated future utilization and display the estimated utilization in predictive graphical user interfaces. In some embodiments, app(s) 254 may configure one or more computer systems to analyze historical patient itinerary data and hospital performance data to identify patterns, trends or correlative relationships in the historical data. For example, trends in historical data may indicate that certain patient diagnoses are associated with certain lengths of stay, or often experience delays and complications in certain portions of the itinerary. Historical data, identified trends and patterns, and correlative relationships may be identified through regression analysis, queuing analysis and other known statistical analysis methods, stored, and recalled to predict future utilization and present the predicted utilization hospital personnel in an easy-to-read graphical interface. Such graphical interfaces may then enable hospital personnel to make more informed decisions based on utilization and capacity and to ultimately provide ever-improving patient care and efficiency. Correlations could be stored, retrieved and processed as Stochastic Information Packets (SIPs), Distribution Strings (DIST) or Stochastic Library Unit with Relationships Preserved (SLURPs). As discussed in further detail below, in some embodiments the implementation of these functions and the advantages realized by the present embodiments are attributed to the use of highspeed data and communication network, as well as personal communication and tracking devices disposed throughout a hospital.

Figure 3:
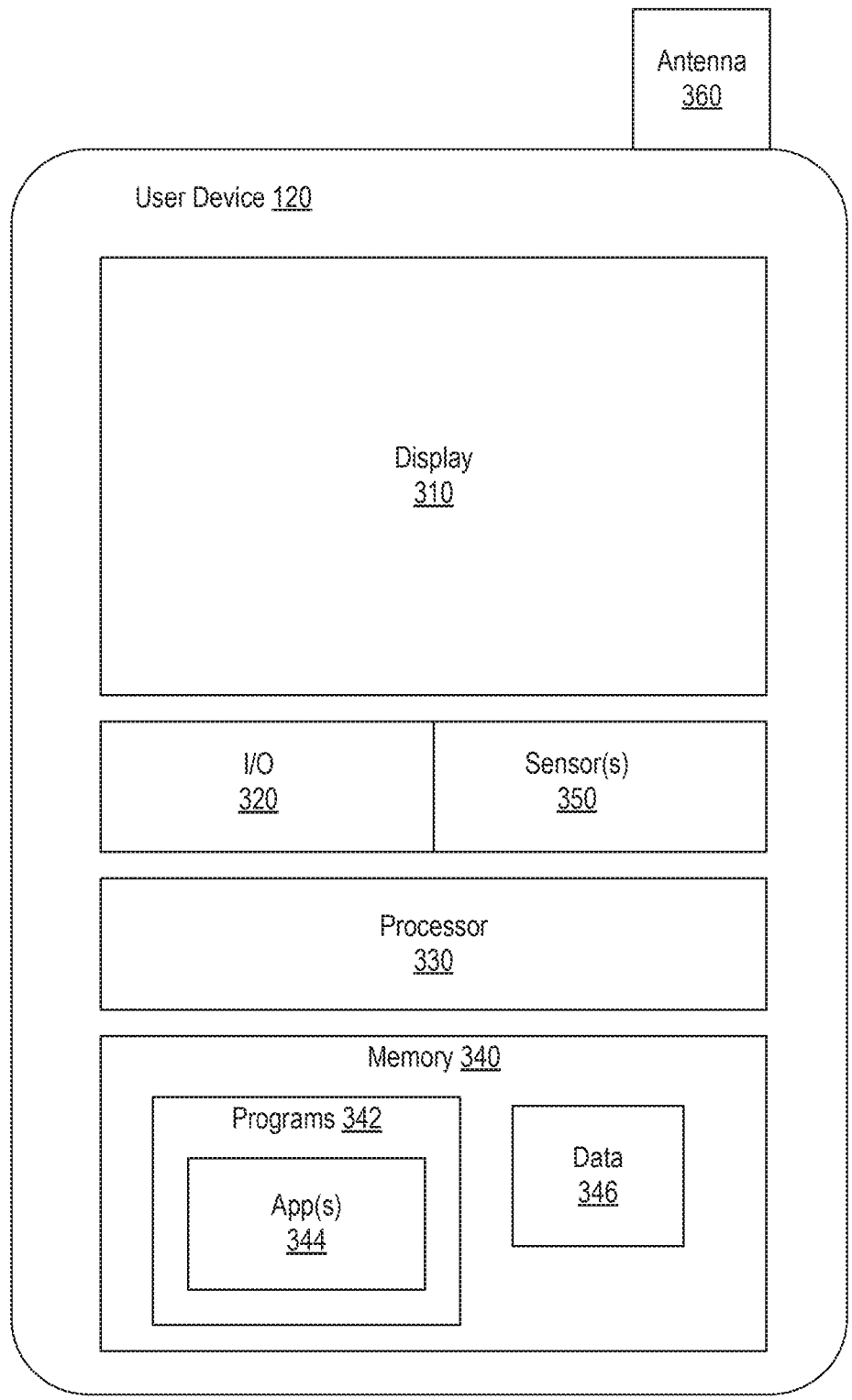
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, air pressure sensors, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
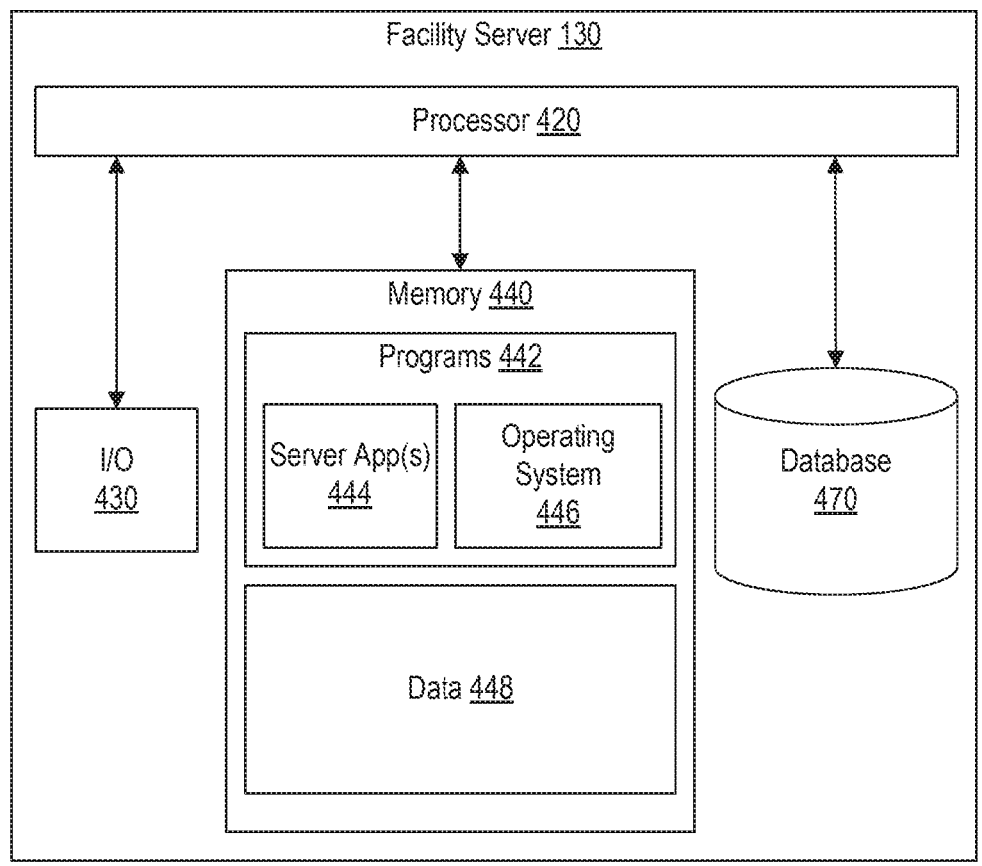
FIG. 4 depicts an example of a facility server, consistent with embodiments of the present disclosure.

FIG. 4 shows a diagram of an exemplary facility server 130, consistent with disclosed embodiments. In some embodiments, facility server 130 may be a local server within facility system 102. In such embodiments, facility server 130 may include one or more distributed computer systems capable of performing distributed computing functions, cloud computing services and functions, and interface-related functions consistent with disclosed embodiments. In some embodiments, facility server 130 may operate in conjunction with network server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a stand-alone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, facility server 130 may connect to multiple facilities located in different geographical locations. In such embodiments, facility server 160 may collect data from multiple facilities to evaluate performance times in different facilities, improve the accuracy of expected completion times for different types of tasks using one or more statistical/data regression algorithms, and predict future utilization of one or more of the facilities.

As shown in FIG. 4, facility server 130 may include one or more processor(s) 420, input/output ("I/O") devices 430, memory 440 storing programs 442 (including, for example, server app(s) 444 and operating system 446) and data 448 (including employee data 449), and a database 470. Facility server 130 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, facility server 130 may also include one or more I/O devices 430 including interfaces for receiving signals or input from devices and providing signals or output to one or more devices that allow data to be received and/or transmitted by network server 160. For example, facility server 130 may include interface components, which may provide interfaces to one or more input devices, such as one or more keyboards, mouse devices, and the like, that enable facility server 130 to receive input from one or more user 125 that is associated with facility system 102.

In some embodiments, facility server 130 may include one or more storage devices configured to store information used by processor 420 (or other components) to perform certain functions related to the disclosed embodiments. In one example, facility server 130 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with facility server 130, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, facility server 130 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, facility server 130 may include memory 440 that may include one or more programs 442 to perform one or more functions of the disclosed embodiments. Moreover, processor 420 may execute one or more programs located remotely from system 100. For example, facility server 130 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of information related to facility utilization such as capacity of various units, census data, and staffing levels, tracking patient statuses such as receiving patient attributes, diagnoses, and conditions, receiving staff schedules and staff skills, receiving one or more hospital rules and legal restrictions, receiving treatment requirements, physicians' orders and regimens associated with patient diagnoses, analyzing received data using one or more rule sets, computer models, or other processing logic, generating data associated with one or more graphical user interfaces, generating one or more communications and/or commands to other computer systems or devices such as user device 120, and updating the graphical user interfaces in real-time based on new data or changes in the analysis results.

In some embodiments, memory 440 may store data 448 including data associated with patients, staff, tasks, assets such as hospital beds, assignment and graphical user interface generation algorithms, historical data, data derived from historical data such as trends, patterns, and correlative relationships. For example, data 448 may include one or more entries including employee data 449 (e.g., identifications of staff, their skill sets, their schedules and availability, staff assignment history), patient medical records, patient assignment history, data associated with patient conditions, data associated with patient treatment plans, patient bed assignments, bed availability, bed locations, bed attributes, hospital rules, established hospital procedures, calculated patient itineraries associated with patient conditions and diagnoses, and legal and restrictions and regulations. Data 448 may also include the current location of the patient, the status of each of the patient physician orders (e.g., lab orders, radiology orders), bed assignment priorities, milestones (e.g., discharge and transfer milestones), transport request status, patient hand-off during shift change, continuity of care data for resource assignments, custom patient attributes, and the real-time statuses of delays or complications in hospital departments and units. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
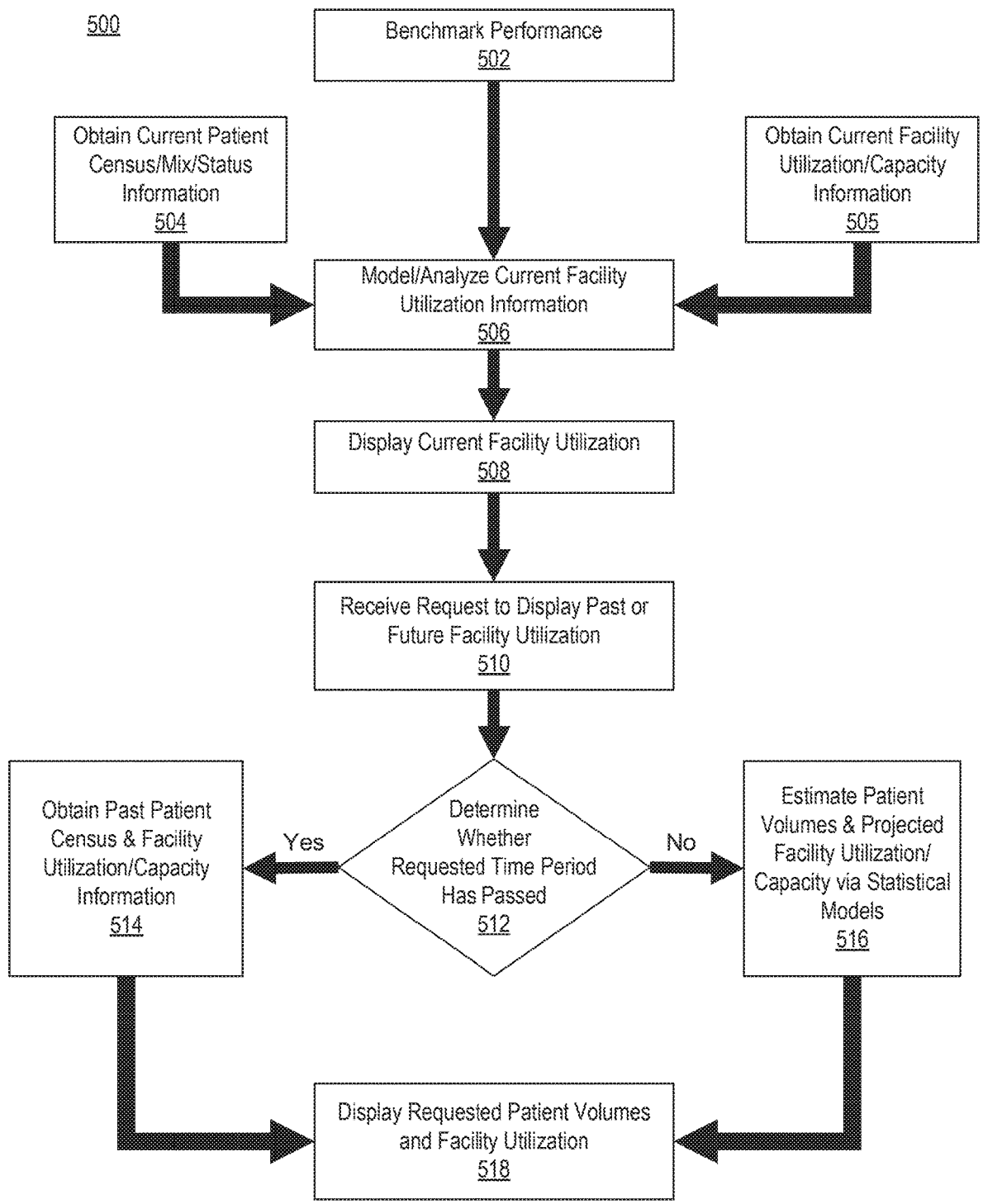
FIG. 5 depicts a flowchart of an exemplary process for generating facility utilization graphical user interfaces, consistent with embodiments of the present disclosure.

FIG. 5 is a flowchart for generating predictive graphical user interface process 500, consistent with embodiments of the present disclosure. As shown, process 500 may include a series of steps including, for example, benchmarking performance in a facility (such as a hospital or group of hospitals) 502, obtaining current facility utilization information 504, displaying current facility utilization 506, receiving a request to display projected future facility utilization 508, estimating projected future facility utilization 510, and displaying projected utilization 512. Process 500 provides medical care facilities and medical care systems, such as hospitals and hospital systems, and/or managed care organizations with a mechanism to understand which resources are being used efficiently, and whether available resources will be appropriate for estimated future utilization. Process 500 is described herein as being performed primarily by facility server 130. In some embodiments, however, one or more computerized devices of system 100 may perform steps of process 1200, as well as any other process disclosed herein. In some embodiments, multiple devices may perform steps of the methods disclosed herein in a distributed computing fashion.

Step 502 may comprise benchmarking the performance of a hospital, group of hospitals or managed care organization. In some embodiments, benchmarking may include evaluating metrics of different departments in a hospital, or different hospitals in a heath care group. Metrics may include quantifiable and qualifiable measures of efficiency and efficacy such as, for example, employee timeliness, likeliness of patient backlog and scheduling congestion, treatment and care timeliness and efficacy, caregiver/staff availability and staffing levels, equipment, supply, and asset levels, hospital bed availability and wait times, transport times between hospital units, and any other measurable metric associated with operations of the medical care facility and the quality of care provided to a patient. In some embodiments, a server such as facility server 130 may compile metric data from a plurality of sources, and continuously or periodically benchmark data for the medical care facility. In some embodiments, user device 120, computer terminal 140, and/or one or more sensor devices (not shown in figures) may continuously provide metric data based on sensed conditions, scheduling information, and input by one or more user 125. In some embodiments, metric data may include historical data previously stored in database 180. Benchmarking step 502 may comprise performing one or more statistical analyses on received metric data, in order to determine the relative performance, congestion, and timeliness of different hospital units and different hospitals, as well as other comparative metrics. In some embodiments, benchmarking step 502 may measure the efficacy of operational elements on patient outcomes, such as readmission rates, mortality rates, or infection occurrences. In some embodiments, benchmarking 502 may include a comparison of performance metrics (such as efficiency, efficacy, congestion, timeliness, etc.) across different operational elements of care within the hospital and throughout a patient itinerary such as transport modes, room occupied, fixed assets encountered, time spent out of patient room. Step 502 may result in creating benchmarking data associated with different departments within a facility, areas within the facility, patient diagnoses, different patient characteristics, and different times of day/week/year.

In some embodiments, step 502 may include combining performance metrics with clinical diagnosis statistics received from one or more third party systems 170 such as a managed care organization, healthcare practice management company, a public database, or a government organization such as Centers for Medicare and Medicaid Services (CMS), Centers for Disease Control and Prevention (CDC), US Environmental Protection Agency (EPA), US Food and Drug Administration (FDA), and any other organization or source of information related to patient diagnosis and care. Clinical diagnosis statistics may represent performance metrics of other hospital hospitals, and facility server 130 may evaluate created benchmarking data against the clinical diagnosis statistics to provide a measure of the hospital's clinical and financial outcomes in relation to other hospitals represented in the clinical diagnosis statistics.

In step 504, facility server 130 may obtain information related to one or more individuals associated with a facility, such as patients currently admitted to a hospital. In some embodiments, current facility staffing information may include staff credentials, skill sets, on call status, and previous workload. Current facility staffing and/or utilization information may be obtained from one or more of memories 250, 340, or 440 or databases 470 or 180. Alternatively or additionally, the current facility utilization information may be obtained via input into administrator terminal 145, computer terminal 140, or user device 120 or via monitoring of sensing devices 147 or patient device 190.

In step 505, facility server 130 may obtain information related to the current patient census, patient mix, or patient status information. In some embodiments, current patient information may include any information or combination of different types of information reflecting the current status of patients of a hospital or healthcare system. For example, current patient information may include information related to a current census, mix, and/or patient statuses, obtained from one or more of memories 250, 340, or 440 or databases 470 or 180.

In step 506, facility server 130 may obtain current facility utilization information. The current facility utilization information may include any information or combination of different types of information reflecting the current status of the facility including patient census data. This may include information related to the current status of admissions, discharges, and capacity (such as, for example, limits and/or constraints on patient numbers or flow). Current patient census information may include information related to patient diagnosis or patient acuity level. The information may be obtained from one or more of memories 250, 340, or 440 or databases 470 or 180. Alternatively or additionally, the current facility utilization information may be obtained via input into administrator terminal 145, computer terminal 140, or user device 120 or via monitoring of sensing devices 147 or patient device 190.

In step 506, facility server 130 may analyze the current facility utilization and/or staffing information. For example, as obtained, current facility utilization information may be assembled in multiple formats, reflect an extended period of time, or be organized based on records associated with particular patients, departments, service lines, or other units within the facility. In step 506, facility server 130 may analyze the information to determine number of patients currently associated with one or more particular departments within the facility. The scope of a department may vary based on a number of factors, such as type of facility, physical layout, and organization structure. Accordingly, department may refer to various units, floors, rooms, locations, functions, and/or statuses within the facility. Step 506 may also include analyzing the current facility utilization information to identify a number of patients that have been transferred between one or more departments in the facility within a particular period of time. Analysis of current facility staffing information may identify patterns and trends in the staffing of individuals with certain skill s or experience and may yield indications of how to optimize staff placement.

In some embodiments, the scope of analyzed information may be defined based on user input or information related to particular inputs or outputs of information. For example, analysis may be governed by filters such as patient source (e.g., a patient from the emergency room department), or filters of a particular granularity, such as the unit level or service line level. In some embodiments, the scope of analyzed information could also be filtered by diagnosis-related group ("DRG"), operating rooms that require specific equipment or apparatuses, rooms that require service, etc.

In step 508, facility server 130 may generate a graphical display of current facility utilization and/or staffing. Any graphical or textual format enabling visualization of facility utilization may be used. In some embodiments, step 508 may comprise generating a diagram, such as a flowchart or Sankey diagram, visualizing a flow and volume of patients through the facility or hospital system.

Figure 6:
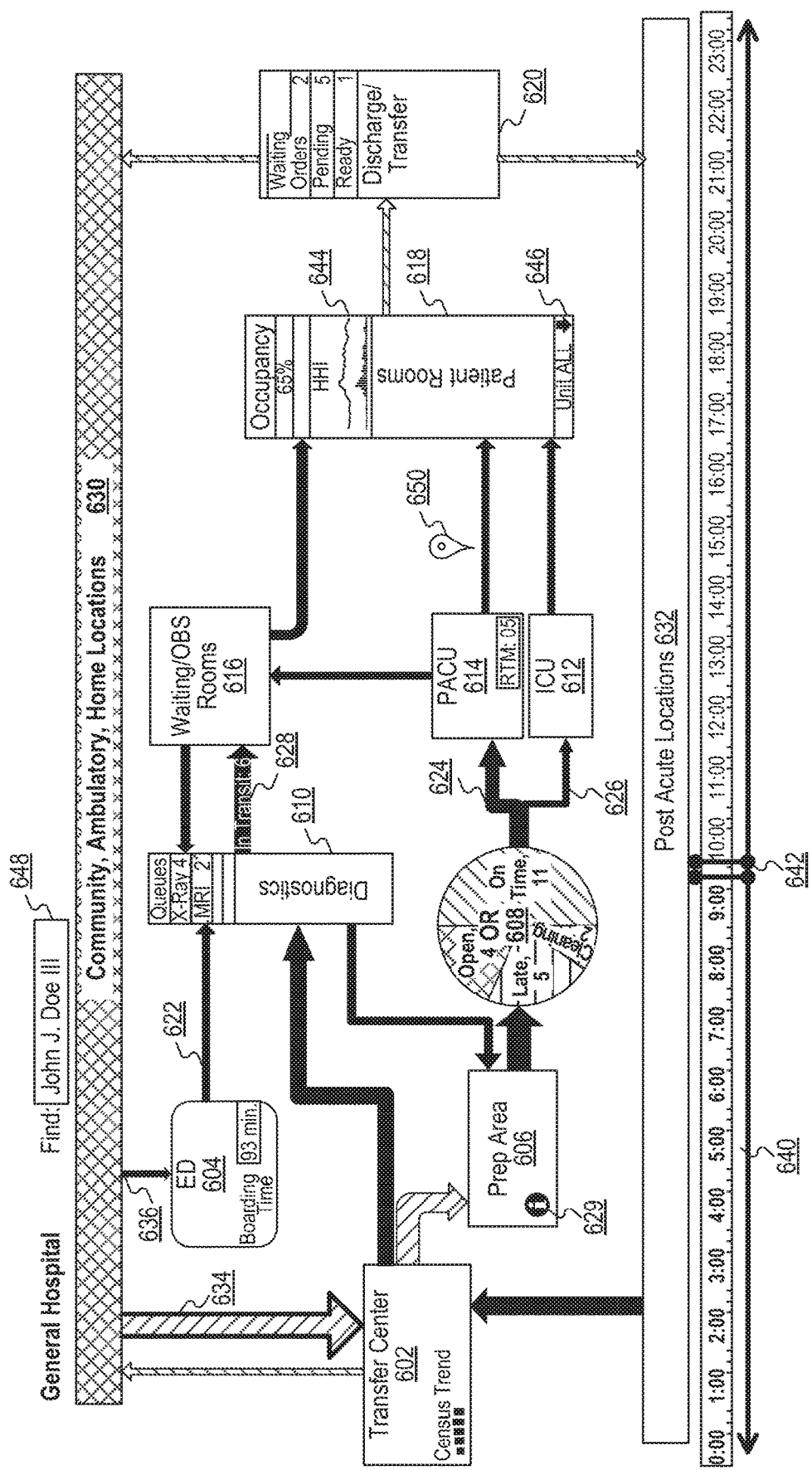
FIG. 6 is an example of a graphical display of current facility utilization, consistent with embodiments of the present disclosure.

FIG. 6 depicts a graphical display of current facility utilization, consistent with disclosed embodiments. Specifically, FIG. 6 depicts a graphical user interface 600 that may be displayed to a user, for example, of computer terminal 140, administrative terminal 145, or user device 120. Interface 600 may include graphical representations of various departments of a facility. As an example, FIG. 6 depicts a number of departments of a hospital, including transfer center 602, emergency department (ED) 604, prep area 606, operating room (OR) 608, diagnostics 610, intensive care unit (ICU) 612, post anesthesia care unit (PACU) 614, observation/waiting areas 616, patient rooms 618, and discharge/transfer 620. In some embodiments, the display depicted in FIG. 6 may be configured to display current facility staffing information.

Interface 600 may include graphical representations of transfers of patients between the represented departments identified in step 506. For example, as shown in FIG. 6, interface 600 may include graphical representations of patients transferred between the departments of the hospital. As in FIG. 6, a number of patients in an emergency room may be transferred from emergency department 604 to diagnostics 610 to receive tests. These transfers may be represented by arrow 622. As another example, patients undergoing surgery in OR 608 may be transferred to PACU 614 at the conclusion of a surgery. Interface 600 may display arrow 624 to represent these transfers. Complications may arise in some surgeries requiring patients to be transferred from OR 608 to ICU 612, and interface 600 may display arrow 626 to represent these transfers.

Representations of patient transfers included in interface 600 may include information related to flow of transfers. For example, in FIG. 6, arrows 622, 624, and 626 are shown in various widths. Such variations in width may represent a quantity/volume of patients transferred during a period of time. For example, the width of arrow 624 may represent a transfer of 20 patients in the previous hour while the narrower width of arrow 262 may represent 10 patients during the same time period. Alternatively, width may represent a number of transfers relative to an ordinary or typical number generated by the benchmarking of step 502. For example, during a given time period the number of transfers from OR 608 to PACU 614 may be equal to the number of transfers from OR 608 to ICU 612. However, this number may be greater than usual for transfers from OR 608 to PACU 614, and thus depicted by a wide arrow, as shown in FIG. 6. Conversely, the number may be fewer than usual for transfers from OR 608 to ICU 612, and thus depicted by a narrow arrow.

The depictions of flow based on width shown in FIG. 6 are merely exemplary. Depictions of patient flow may be displayed in interface 600 based on any number of visual attributes such as color, pattern (as shown in arrow 634), animation, or textual annotation. Further a combination of attributes may be employed to depict multiple measures of patient flow. For example, in some embodiments, width may be used to show the number of patients transferred between two departments over a given period of time, while color may be simultaneously used to show how that number compares to an ordinary or typical number. As another example, some embodiments may use textual overlays, as shown in arrow 628, to indicate patient flow.

The graphical representations of departments may include additional graphical elements indicative of current utilization. Utilization information related to the departments may be shown based on any number of visual attributes such as color, pattern, animation, size, or graphical and/or textual annotation. For example utilization of a department may be shown by adjusting the size of its representation in interface 600. In FIG. 6, transfer center 602 is displayed as a larger rectangle than prep area 606. This may indicate that transfer center 602 is currently occupied by a greater number of patients or operating at a greater percentage of its capacity than OR 608. In some embodiments, graphical representations of departments may be annotated with various information related to indicate utilization of the respective department such as trends of key performance indicators or indications that the department is at capacity, below an ordinary utilization, or operating behind schedule.

FIG. 6 shows exemplary annotations, such as textual indications of boarding time, occupancy, or status overlaid on the graphical representation of a department (as shown with respect to ED 604, diagnostics 610, PACU 614, patient rooms 618, and discharge/transfer 620). For example, annotations may be displayed to indicate metrics associated with particular departments. As shown in FIG. 6, occupancy information is textually displayed in association with patient rooms 618. As another example, an indication of a number of patients ready to move (RTM) is displayed in association with PACU 614. In some embodiments, an icon indicating that additional information is available may be displayed in association with a department, such as icon 629 related to prep area 606. Other sources of information, such as pie charts, heat maps, and sparkline charts could be displayed in association with graphical representations of departments. For example, FIG. 6 includes chart 644 displayed in association with patient rooms 618, a pie chart displaying a breakdown of patient/room statuses within OR 608, and a bar graph displayed in association with transfer center 602 indicating a census trend over time. Chart 644 includes a line graph showing changes in hand hygiene index (HHI), a metric used to gauge hand washing compliance by care givers.

Interface 600 may also include graphical representations of patient flow in and out of the facility. FIG. 6 depicts representations of community 630 and post-acute care 632 along with arrows 634 and 636 depicting the flow of patients into the facility from the community and arrow 638 depicting the flow of patients into the facility from post-acute care. Graphical representations of patient flow in and out of the facility may include any of the attributes described above with respect to patient flow between departments.

Interface 600 may also include a graphical indication of the time currently shown in the interface. For example, FIG. 6 includes a timeline 640 and slider 642. Timeline 640 may include graduated indications of time within any desired range, such as minutes, hours, days, etc. Slider 642 may indicate the time currently being depicted by interface 600. In FIG. 6, slider 642 indicates the interface 600 currently reflects the utilization of the facility at 9:30 a.m. The period of time reflected by interface 600 may be a fixed or adjustable time period before the time indicated by slider 642. Alternatively, the period of time reflected may be represented by the width of slider 642.

Figure 7:
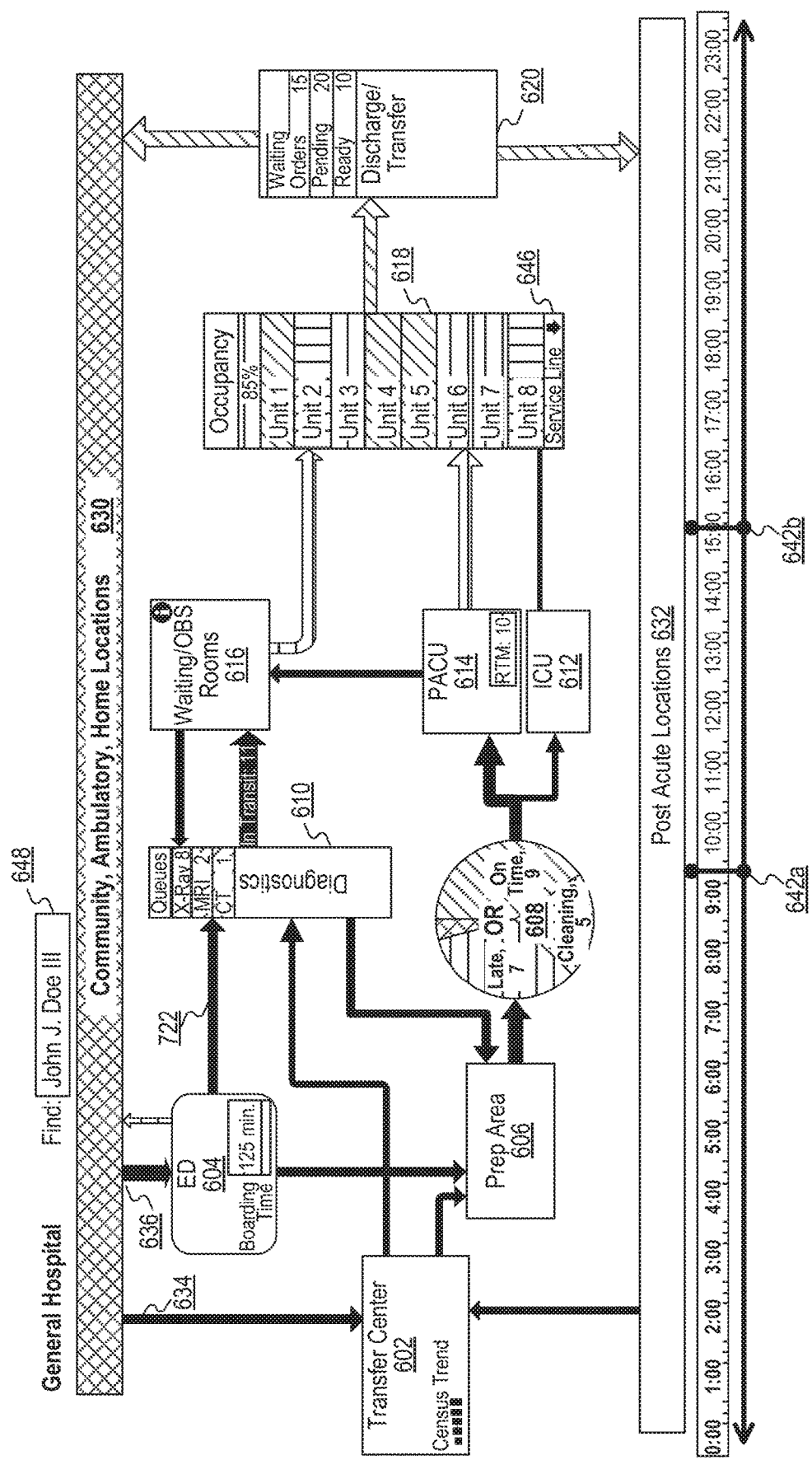
FIG. 7 is an example of a graphical display of projected facility utilization, consistent with embodiments of the present disclosure.

Referring back to FIG. 5, in step 510, facility server 130 may receive a request to display past or future facility utilization and/or staffing information. As shown in FIG. 7, interface 600 may receive input from user 125 moving slider 642 to select a requested time for display. Additionally or alternatively, interface 600 may receive the request via one or more textual fields, dials, buttons, or any other known means of receiving a selection from user 125. Various embodiments may restrict selection to within a particular amount of time before or after the current time or may allow entry of any time.

In step 512, facility server 130 may determine whether the time period reflected in the request to display past or future facility utilization information has already passed. For example, server 130 may compare the requested time to the current time. Alternatively, server 130 may receive a selection from user 125 indicating whether the request is a request for a past time period or a future time period.

If facility server 130 determines that the requested time period has passed, process 500 may proceed to step 514. In step 514, facility server 130 may obtain past facility utilization information. This information may be retrieved from any combination of the sources noted with respect to step 504, and may be retrieved from the same source as previously retrieved in step 504 or from a different source or sources based, for example, on procedures for archiving past information.

Alternatively, if in step 512 facility server 120 determines that the requested time period has not passed, process 500 may proceed to step 516. In step 516, facility server 130 may estimate patient volumes and projected facility utilization for the time period set by the request. The estimated facility utilization may include an estimated future value of any piece of information obtained or displayed in steps 504 or 506 above. Further, facility server 130 may estimate the projected facility utilization based on any combination of information stored in any of the sources noted with respect to step 504. For example, the estimated utilization may be based on the performance benchmarks of step 502, patient census data (including patient DRG/Acuity Mix), physician orders, and/or service line assets such as staffing, equipment, or materials.

Facility server 130 may estimate projected utilization based on information of any level of generality or specificity. For example, projected utilization may be estimated based on expected time that individual patients will spend at particular departments within the facility or based on patients' current department, status, location, medical history, pending orders, personnel needs, and equipment needs. Additionally or alternatively, facility server 130 may estimate projected utilization based on ordinary expected outcomes of the number of patients currently associated with the departments of the facility. Such ordinary expected outcomes may comprise mean or median numbers, and may incorporate variance metrics associated with such statistics. Further, projected utilization may be estimated based on one or more anticipated flow path(s) through the facility and may employ statistical models such as Monte Carlo and discrete event simulations.

Additionally or alternatively, facility server 130 may estimate projected utilization based on current census information, patient DRG mix and acuity levels on an aggregated scale, incorporating the effects of various combinations of such information on utilization, throughput expectations and capacity constraints.

In step 516, facility server 130 may estimate multiple potential projected levels of facility utilization. In an embodiment, facility server 130 may estimate an expected outcome, a "worst-case" scenario outcome, and a "best-case" scenario outcome. Worst-case and best-case may be related to any number of undesired or desired scenarios such as lack of available capacity, too much available capacity, imbalance of patient flow between departments, or other scenarios. Best-case and worst-case scenarios may be calculated based on probability. For example, server 130 may estimate an expected utilization, along with a low utilization and a high utilization. The low and high utilizations may be estimated based on absolute possibilities given existing conditions, or by a set or adjustable standard deviation.

In step 518, facility server 130 may display the projected facility utilization. As shown in FIG. 7, the projected utilization may be displayed in via interface 600 in a manner similar to the display of current facility utilization information, as described above. In an embodiment, slider 642 may split into a base 642a and a pointer 642b. Base 642a may indicate the current time, for example 9:00 a.m. as shown in FIG. 6. The pointer may indicate the time shown in the projected utilization display, for example 13:00 (or 1:00 p.m.) as shown in FIG. 6. In FIG. 7, arrow 722 may depict a projected number of transfers between ED 604 and diagnostics 610. Arrow 722 is displayed wider than arrow 622 in FIG. 6. This could indicate that a greater number of transfers are expected at 13:00 than at 9:00.

In some embodiments, step 514 may include displaying information indicating differences between current utilization and projected future utilization. For example, arrow width may indicate number of patients expected to be transferred between two departments within a given period of time in the future, while arrow color may indicate whether the projected number is greater or fewer than the number of patients transferred between the two departments over the same amount of time immediately prior to the present time.

Figure 8:
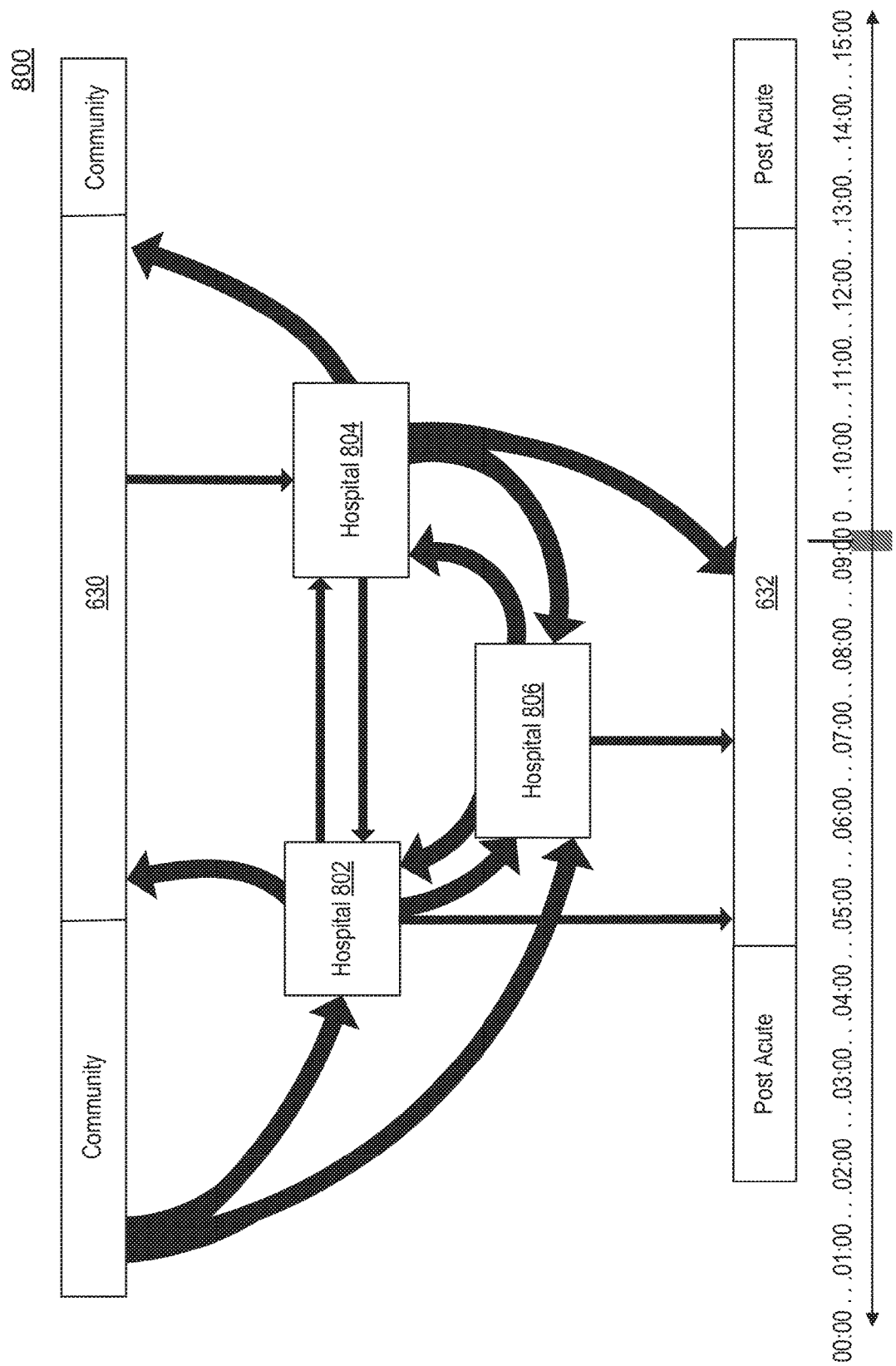
FIG. 8 is an alternative example of a graphical display of facility utilization, consistent with embodiments of the present disclosure.

While the embodiments described above were directed to departments within a facility, the present disclosure is not limited to such departments, and utilization of other subdivisions within a facility or organization may be displayed. FIG. 8 depicts an interface 800. Interface 800 comprises a graphical display of current facility utilization, similar to the display of FIGS. 6 and 7. However, instead of departments, interface 800 depicts graphical representations of three hospitals, hospital 802, 804, and 806. Interface 800 may display any of the past, present, or future patient utilization information discussed above with respect to hospitals 802, 804, and 806.

Figure 9:
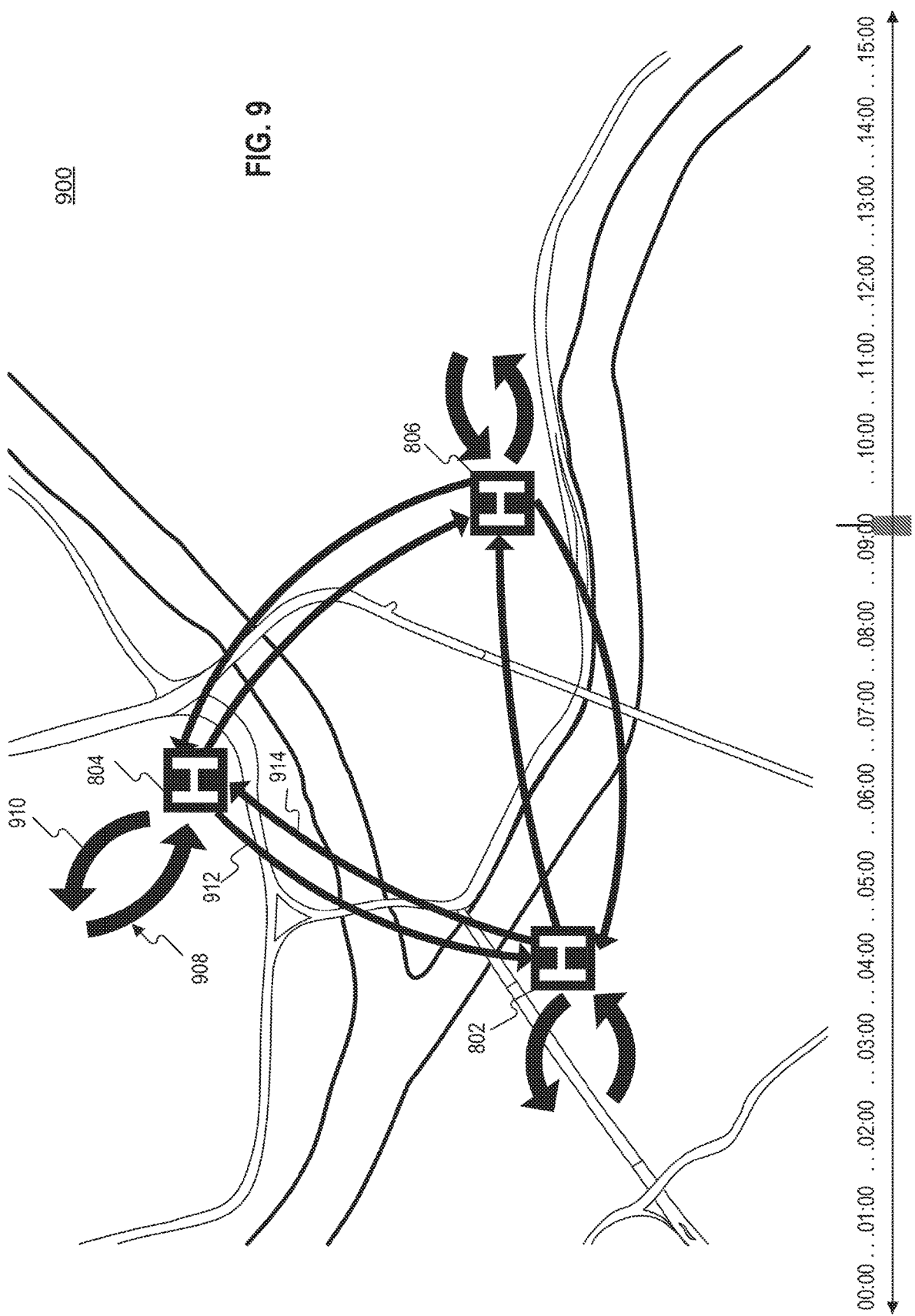
FIG. 9 is another alternative example of a graphical display of a facility utilization, consistent with embodiments of the present disclosure.

In some embodiments, utilization may be displayed in relation to physical locations. FIG. 9 depicts an interface 900. Interface 900 comprises a graphical display of facility utilization of hospitals 802, 804, and 806. In interface 900, hospitals 802, 804, and 806 are shown on a map based on the physical location of the hospitals. The map displayed in interface 900 may be stored in any of the locations discussed above for utilization information or may be retrieved separately from a third-party mapping service such as Google Maps, Bing Maps, or Mapquest. Interface 900 may include graphical representations of patient flow between hospitals, such as arrows 912 and 914, and graphical representations of patient flow between the hospitals and the community, such as arrows 908 and 910. In some embodiments, graphical representations of patient flow between hospitals may include additional or more specific information. For example, arrows such as 908 and 910 may be overlaid with text or other information indicating the number of patients currently in transit or who have taken the identified path within a particular period of time. Filters, similar to those described above with respect to step 506, may be provided to restrict interface 900 to particular information such as a specific diagnosis-related group, isolation cases, etc.

In some embodiments, facility server 130 may receive a selection, such as a mouse click, of a graphical element in interface 600, 800, or 900. In response to the selection, facility server 130 may provide instructions to display additional or more specific information related to the selected element. For example, in response to a selection of a department or hospital (such as ED 604 in FIG. 6 or Hospital 802 in FIGS. 8 and 9), facility server 130 may provide instructions to display additional/alternate information or a popup window including more information than could be included in the graphical representation itself. As shown in FIG. 6, an arrow 646 is displayed within patient rooms 618. Facility server 130 may receive a selection of arrow 646, and in response display information within patient rooms 618 related to patient rooms within individual units, as shown in FIG. 7. Further, in response to selection of an arrow (such as arrow 622 in FIG. 6, arrow 722 in FIG. 7, arrow 908 in FIG. 9), facility server 130 may provide instructions to display additional information related to the transfer of patients depicted by the arrow.

In some embodiments, interfaces such as interface 600, 800, or 900, may include a search field, such as search field 648 shown in FIGS. 6 and 7. Facility server 130 may receive information identifying a patient into the search field, such as "John J. Doe III." In response, facility server 130 may generate instructions to display an indication within the interface of the identified patient's status within the facility. This indication could be displayed in a number of ways, such as highlighting or flashing a representation of a department, or by displaying a marker, such as marker 650 shown in FIG. 6.

In some embodiments, interfaces such as 600, 800, or 900, may be configured to display a nursing unit health score indicative of the performance and efficiency of one or more hospital units. Facility server 130 may receive information identifying one or more hospital units and a period of time, input by a user. In response, facility server 130 may generate instructions to display the nursing unit health score within the interface. A user may input one or more values associated with the nursing unit health score such as, patient population, nursing roster, and/or staffed bed availability to observe how changes in one or more of these factors may influence the nursing unit health score.

Interfaces 600, 800, and 900 may be used together. For example, facility server 130 may receive a selection of a level of specificity or "zoom" level desired, and alternative between interfaces such as interfaces 600, 800, and 900 to reflect different levels of zoom. For example, facility server 130 may receive a selection of hospital 804 in interface 900. In response to the selection, facility server 130 may provide instructions to display interface 600, including the departments within hospital 804. In some embodiments, this functionality may be integrated with a mapping application such that when a user zooms into a facility beyond a set level, server 130 will provide instructions to change from a map view such as interface 900 to a departmental view such as interface 600.

In some embodiments, one or more graphical user interfaces generated by the disclosed systems may calculate and provide for display a nursing unit health score. The health score may incorporate multiple real-time data points and reduce large amounts of data to a simple metric that is easy for a viewer of the graphical user interface to understand and make swift administrative decisions. Thus, the generation and display of a nursing unit health score may better enable hospital administrators to more efficiently staff a hospital or hospital unit. In some embodiments, a hospital administrator may include a change nurse, a placement nurse, a clinician, general administrative staff, and/or support staff. As described herein, a nursing unit health score is a metric representative of the efficiency of a nursing unit at a given time as well as the workload on the staff and the resource burden on the respective unit. In some embodiments, disclosed systems may generate and display a predictive nursing unit health score to give administrators the ability to manage and plan based on both realtime and forecasted information reflective of a hospital unit's capacity and demand. Additional advantages may include, for example, improved visibility into transportation and bottlenecks, improved alignment of staffing capabilities with unit and patient needs, and/or improved insight into future demand within the unit. Thus, the disclosed embodiment provide specific means for processing large amounts of data from multiple sources, and providing new graphical user interfaces that provide a viewer with calculated metrics representative of the collected real-time data, or predictive metrics representative of collected real-time and historical data, to provide calculated metrics for potential scenarios or at selected future points in time.

In some embodiments, the nursing unit health score may be a combination of metrics surrounding staffing, resource utilization and capacity. Examples could be physical bed availability, staffed bed availability, nursing roster, staff skill set, current or historical census data, unit churn, aggregated patient acuity, and patient mix. When the metrics or dimensions (or the combination of certain metrics or dimensions) exceed specified thresholds, notifications and/or recommendation for action are triggered. These metrics may be collected using one or more computerized systems in the facility or in communication with systems in the facility such as, for example, a capacity management system, a patient placement or hospital bed tracking system, a statistical analytics system, and/or an admission/discharge/transfer tracking system. In some embodiments, such computer systems may receive inputs from sources such as emergency department direct admit, i.e., information on patients from doctor's offices, clinics, tele-health systems, skilled nursing, behavioral health facilities, long-term care facilities, etc., post-anesthesia care units, post-op care units, and other external sources.

In some embodiments, disclosed systems may utilize recorded census data for a particular unit, to determine a nursing unit health score. Census data may be generated by or received via a capacity management system for monitoring resource utilization of different units in a hospital, such as a number of hospital beds that are occupied. In some embodiments, census data may include predictive values forecasts a census value for a particular unit, or area, within a facility, such as an intensive care unit, a cardiac unit, surgery, etc. A census value may account for patient intake and discharge, staffing schedules, and bed availability. In some embodiments, census data may include information associated with a time period prior to a patient's hospital admission, such as registration data, lab orders, doctor referrals, diagnosis upon admission, preadmission data, bed or staff availability, family contact information or medical history information, bed or staff assignment, and schedules associated with the patient. In some embodiments, census data may include data recorded and stored in a networked database a reflective of events during a patient's hospital stay such as acuity assessment data, identification data, diagnostic data and procedure data, review/adjustment of staffing levels and assignments, other patient admission/discharge/transfer data, staff shift changes and staff handoffs between nurses, assets utilized, released, and added, patient rounds, staff breaks, orders to transfer patients, and length of stay updates. In some embodiments, census data may also include pending discharge status, discharge order, discharge planning, and push for bed placement.

As referenced herein, a nursing roster may include information such as individual staff member credentials, skill sets, work schedule information, and/or historical workload assignment. This information may provide hospital administrators with the ability to efficiently and strategically staff hospital units with staff having skill sets or experience that is in higher demand for that particular unit.

Unit churn data may correspond to a number of patients admitted, transferred, and/or discharged within a particular unit of time. For example, unit churn may be calculated for an hour, day, week, etc. Patient acuity refers to the severity of a patient's diagnosis. In the aggregate, this may be the average acuity level of patients in a particular unit. Patient mix may refer to the mix of patients based on the population of patients admitted at a given time. Patient mix information may include descriptive and/or diagnostic characteristics such as acuity level, diagnosis, weight, gender, psychosocial needs, etc.

In some embodiments, disclosed systems may calculate a nursing unit health score based on a computer model created and trained using one or more of the metrics described above. In some embodiments, metric data may be received from one or more hospital systems in response to one or more queries generated by system processors, or automatically by "push" updates from networked computer systems. In some embodiments, disclosed systems may aggregate metric data, and apply one or more algorithms to normalize aggregated data, to conform to a uniform scale having an upper and lower threshold. Disclosed systems may then calculate the nursing unit health score using the normalized metric data in conjunction with one or more computer models or algorithms to apply a weighting factor to different metrics of the normalized metric data.

In some embodiments, a weighting value applied to each metric may be optimized by performing a sensitivity analysis using sample or observed data. In some embodiments, a user may be able to adjust the weights in real-time.

In some embodiments, disclosed systems may generate a graphical user interface element for displaying the nursing unit health score to a user, e.g., hospital administrator, via a graphical user interface. As previously discussed, the nursing unit health score may provide information to a hospital administrator indicative of the current status of a nursing unit including efficiency, workload burden, and/or predicted efficiency or workload burden. Thus, a low score (e.g., a score below a predetermined threshold for a certain unit and over a particular time period) may indicate to a hospital administrator that, for example, staff should be redistributed or that the unit staff is operating over capacity. By including nursing roster information, the score may aid hospital administrators in better assigning staff based on skills or previous experience.

As previously discussed, in some embodiments, disclosed embodiments may calculate and provide for display a nursing unit health score calculated for a future time, to serve as a predictive indicator of the staff that will be required for a future time period or for a certain expected scenario. For example, if a city is expecting an influx of people for an event such as a sporting event, the disclosed embodiments may apply a predictive computer model trained with exemplary parameters associated with the sports event, such as a predicted increase in population. The trained predictive model may be applied to analyze real-time metric data, to generate a predictive nursing unit health score for the potential future event based on current conditions. In this example, the nursing unit health score may indicate that more staff will need to be scheduled for a shift during the sporting event.

As another example, a computer model may be trained with different data sets associated with different seasons of the year. In practice, some metrics may provide better indicators of efficiency and burden depending on the time of year and associated climate conditions. Thus, some embodiments of the disclosed systems may automatically select different computer models having different predetermined or trained metric weighting, to calculate and provide for display nursing unit health scores that reflect the most relevant metric data for the given time period. In this example, the nursing roster may be assigned a different weight during the winter as a result of decreased staff availability during the holidays. The predicted nursing unit score may aid hospital administrators in preparing for changes in staffing or patient intake. In another example, changes in patient mix may occur, e.g., an outbreak of a condition, such as rhinovirus, may alter the patient mix, triggering a change in the observed or predicted health score.

Figure 10:
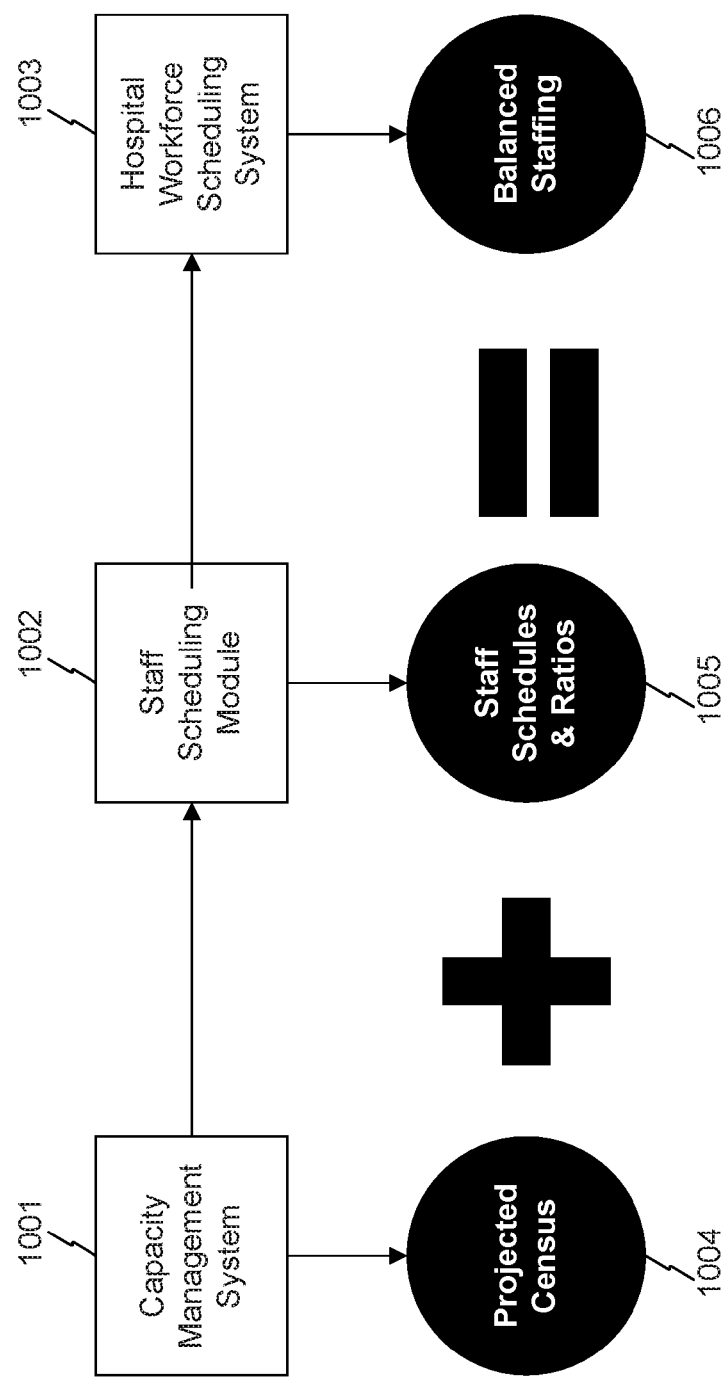
FIG. 10 illustrates an example overview of a hospital workforce scheduling system, consistent with embodiments of the present disclosure.

At a high-level, the integration of data sources (projected census values, staff availability, recommended staff levels for a unit, etc.) is illustrated in FIG. 10. In the example illustration a capacity management system 1001 provides a projected census value 1004. For example, a projected census value 1004 may be calculated using data available regarding the current status (e.g., current census) as well as projected values given impending or confirmed transfers, admissions, etc., as well as times associated therewith.

By way of specific example, a projected census value 1004 may be determined by an embodiment using input data from a capacity management system including, but not necessarily limited to, a number of physical beds in a unit, a current census value, a pending discharge status, a confirmed discharge status, a pending transfer out value, a pending transfer in value, a preadmission value, as well as clean beds, dirty beds and blocked beds values. Thus, an embodiment may calculate, e.g., in three hours' time, a projected census value (i.e., the number of patients expected to be in a given unit, e.g., surgery or intensive care).

A staff scheduling module 1002 for its part may be configured to output appropriate staff schedules and ratios 1005. For example, a predetermined staff scheduling ratio may be implemented such as one assigned nurse to three occupied beds. Given this information, the staff scheduling module 1002 outputs a proposed staff schedule, e.g., one that accommodates a predetermined staffing ratio for a unit or area with a given number of beds. The staff scheduling module may include information on staff credentials, skill sets, and prior experience.

In an embodiment, the actual, available staff capable of working in a unit or area during a given shift is available to a hospital workforce scheduling system 1003. In an embodiment, having the projected census value for a hospital area 1004, the staff schedule and ratio values for the area 1005, as well as access to available staff data, a balanced staffing plan 1006 may be output. This balanced staffing plan 1006 accounts not only for current census, but also considers that projected census value and adjusts staff scheduling recommendations to meet these projected needs.

Figure 11:
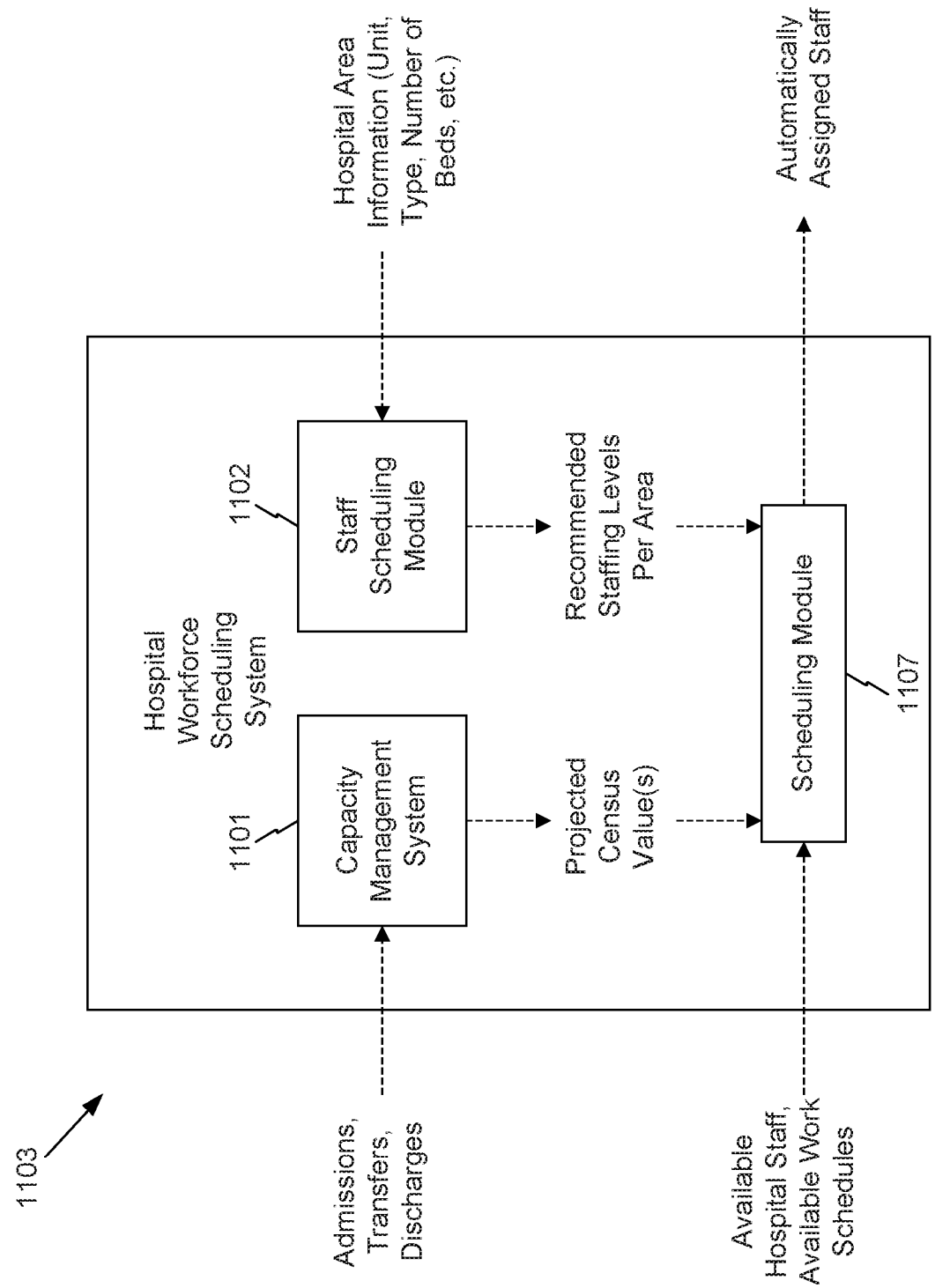
FIG. 11 illustrates an example system for automated hospital workforce load driven scheduling optimization, consistent with embodiments of the present disclosure.

FIG. 11 illustrates an example workforce scheduling system 1103 according to an example embodiment. Here, a capacity management module 1101 takes as input available data used to create a projected census value, e.g., admissions, transfers, discharges, etc., as described herein. A staff scheduling module 1102 takes as input available data used to create recommended staffing levels generally per area, e.g., one nurse assigned to three beds, etc. For example, hospital area information may be input to the staff scheduling module, e.g., a number of physical beds less a number of blocked beds for a particular hospital unit, as well as predetermined data regarding a staff to bed ratio, such as 3:1 by way of non-limiting example.

In an embodiment, the workforce scheduling system 1103 may also output a nursing unit health score indicating the efficiency of a nursing unit. As previously described, this score may be calculated using data collected from the staff scheduling module 1102 and capacity management module 1101, as well as other internal, external, or third-party systems.

Given the projected census value for a hospital area and a recommended staffing level for the hospital area, as well as the physical attributes of the unit and available workers, a scheduling module 2007 coordinates this information with available hospital staff and scheduling information to automatically produce a balanced staffing plan, e.g., including automatic assignment of staff to particular beds in a unit for an upcoming shift.

Figure 12:
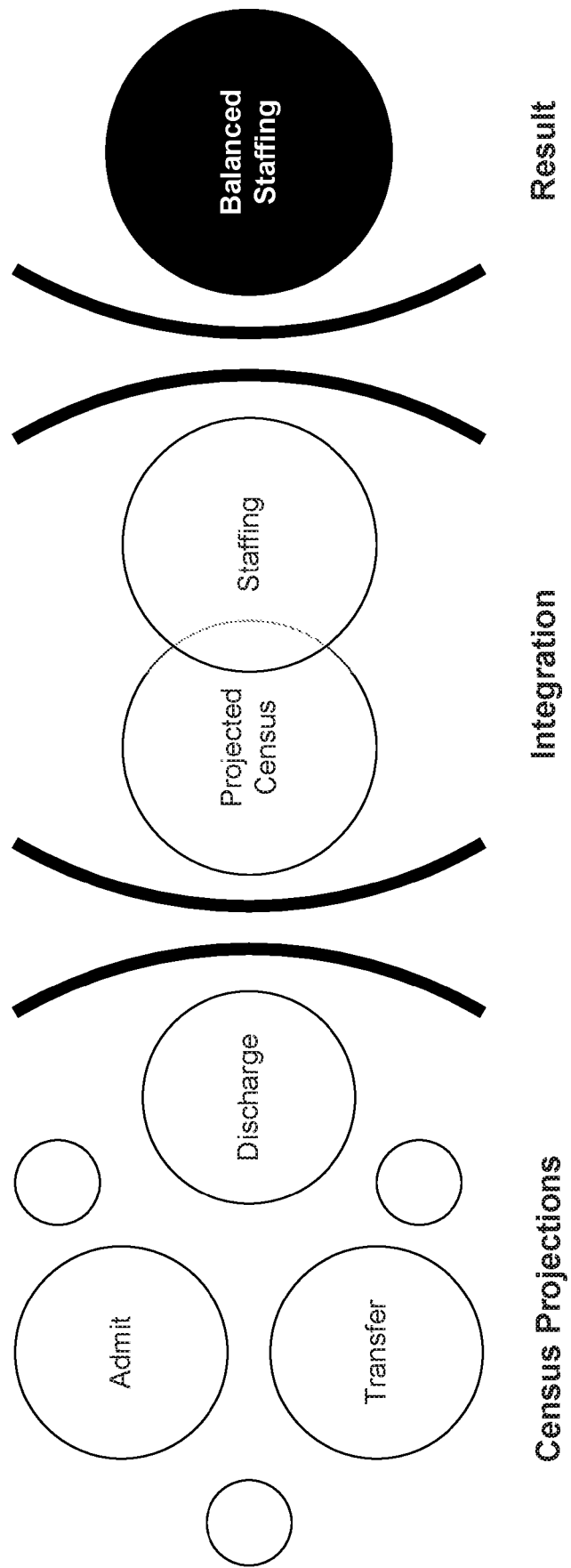
FIG. 12 illustrates an overview of integrating census projections and available staffing for balanced staffing plans, consistent with embodiments of the present disclosure.

This is illustrated in a generalized view in FIG. 12. As shown, the census projections are integrated into staffing data in order to achieve balanced staffing for a future work time. Thus, census projections derived from admission, transfer and discharge data are used to match available staff to projected needs of a hospital unit or area automatically.

Figure 13:
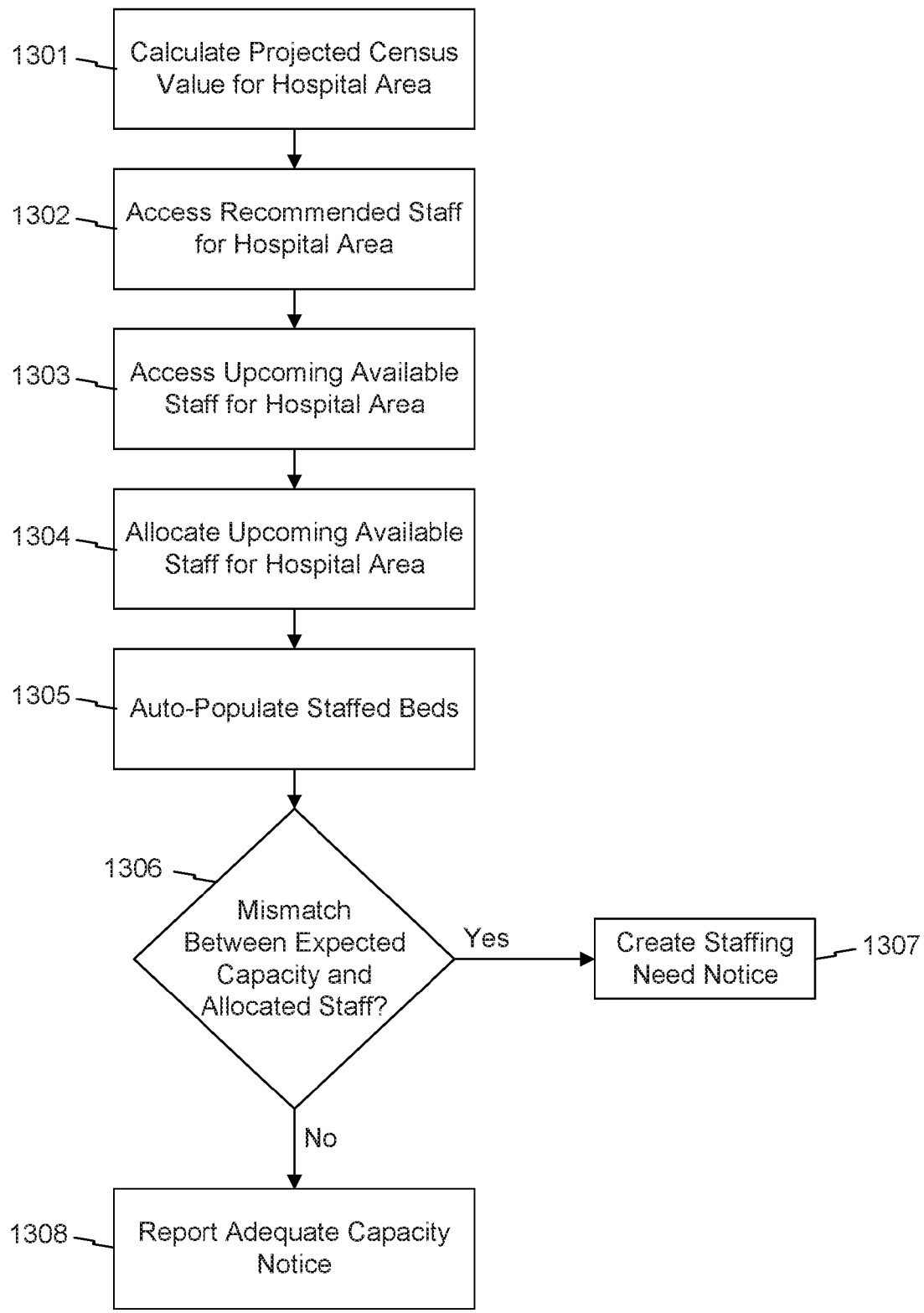
FIG. 13 illustrates an example method for automated hospital workforce load driven scheduling optimization, consistent with embodiments of the present disclosure.

An example method of automatically producing a balanced staffing plan is illustrated in FIG. 13. In the illustrated example, an embodiment calculates a projected census value for a hospital area at 1301. Again, this may include predicting an expected number of patients for the unit in question given current census data, pending discharges and transfers, expected admissions, etc.

An embodiment then accesses recommended staff for the hospital area at 1302, e.g., a number of staff currently recommended for projected census value. This permits a match between projected need (represented by the projected census value) and available staff, rather than a match between a less relevant data set, e.g., physical beds in a unit and/or a current census value. Moreover, this avoids the all too common situation where a hospital fills physical beds and then reactively attempts to find staff to accommodate the filled physical beds.

The upcoming available staff for the hospital area, e.g., workers currently scheduled to work an upcoming shift within the hospital unit, is accessed at 1303. This permits an embodiment to allocate the actual staff available for a shift in a unit or area of the hospital with the projected census in mind at 1304. This likewise permits an embodiment to auto-populate parameters within a management system at 1305, e.g., assign workers to staffed beds, identify excess staffed beds (projected empty staffed beds), etc.

Further, an embodiment provides a proactive monitoring and resolution capability. As illustrated in the example of FIG. 13, an embodiment may be utilized to determine at 1306 if there exists a mismatch between an expected capacity (e.g., as represented by the projected census value for a hospital area or unit) and allocated staff (e.g., available staff scheduled to work in a hospital area or unit) as compared with a preferred or required staffing ratio, e.g., three (3) beds assigned per nurse.

If so, an embodiment may automatically generate a notification at 1307, e.g., a staff need notification. This notification may be displayed locally (e.g., on a display screen operatively coupled to the system) and/or communicated to remote devices, e.g., mobile units such as smart phones of available or scheduled workers.

This permits a user, e.g., hospital area unit manager, to anticipate that the unit might be understaffed given the currently available workers scheduled to the unit or area, given the projected census value for that unit or area of the hospital. As may be appreciated, this also permits automated messaging, e.g., communications with other possible workers regarding an impending or expected need for additional capacity or workers. The converse is also true, e.g., an expected over-supply of workers or overstaffing situation may be anticipated, and scheduling of workers adjusted accordingly.

Figure 14:
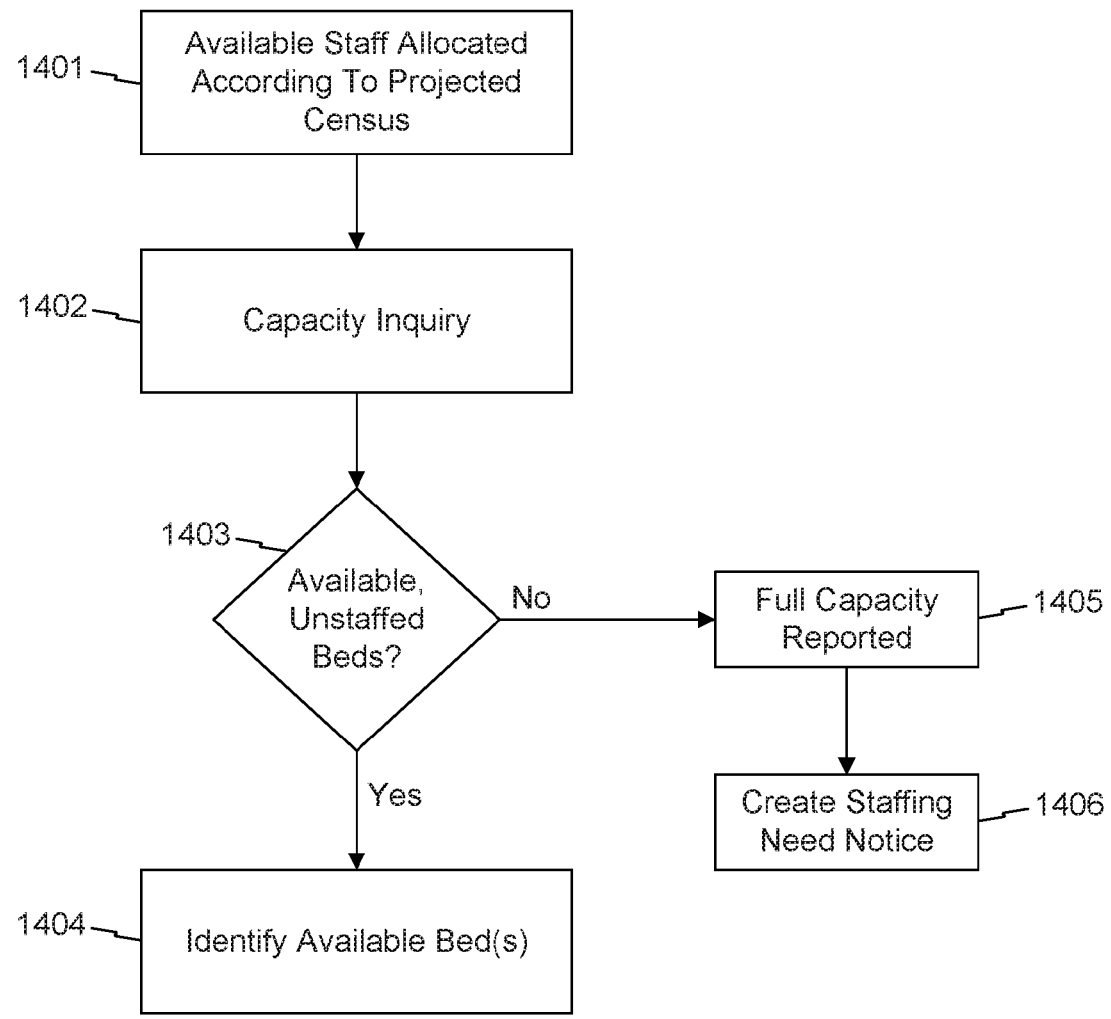
FIG. 14 illustrates an example method for automated bed assignment using a system for automated hospital workforce load driven scheduling optimization, consistent with embodiments of the present disclosure.

In addition, and referring to FIG. 14, an embodiment may be used to more accurately calculate projected bed assignments. This is by virtue of an embodiment producing a more realistic scheduling assessment given the projected census number.

By way of example, the available staff is allocated to an area or unit of the hospital according to the projected census number at 1401, as described herein. If a capacity inquiry is received at 1401, e.g., a user searches for a particular bed type, in a particular unit, etc., an embodiment may use the projected staff allocations, down to the bed level, to determine at 1403 if there will be such a staffed bed available within the unit. That is, an embodiment will answer a query regarding the capacity check not simply with the data regarding physically available beds within a given unit or area, but will report whether or not a staffed bed in that unit or area will be available at the appointed time. If so, an embodiment may report back the available bed(s) at 1404, e.g., bed number(s) and/or location(s). However, if a staffed bed is not projected as available, as determined at 1403, an embodiment may output a full capacity notification or report at 1405, as well as create a staffing need notification at 1406. In this way, a user (e.g., area or unit manager) will have easy access to projected staffed bed availability within a unit in time to adjust staffing allocations.

An embodiment therefore integrates a projected census value with recommended/preferred staffing levels and data regarding actually available staff to create a balanced staffing plan. Given this forecasting availability, shortfalls and excesses regarding staff allocations can be identified early enough that remedial actions are available.

It will be appreciated that an embodiment may be implemented using a variety of types of computing devices. Such devices might take the form of a work station, a laptop computer, a hand held or mobile computer, e.g., a smart phone or tablet computing device, as well as combinations of the foregoing. The computing device(s) utilized for implementing the workforce management technology described herein may include a variety of circuitry and components.

Figure 15:
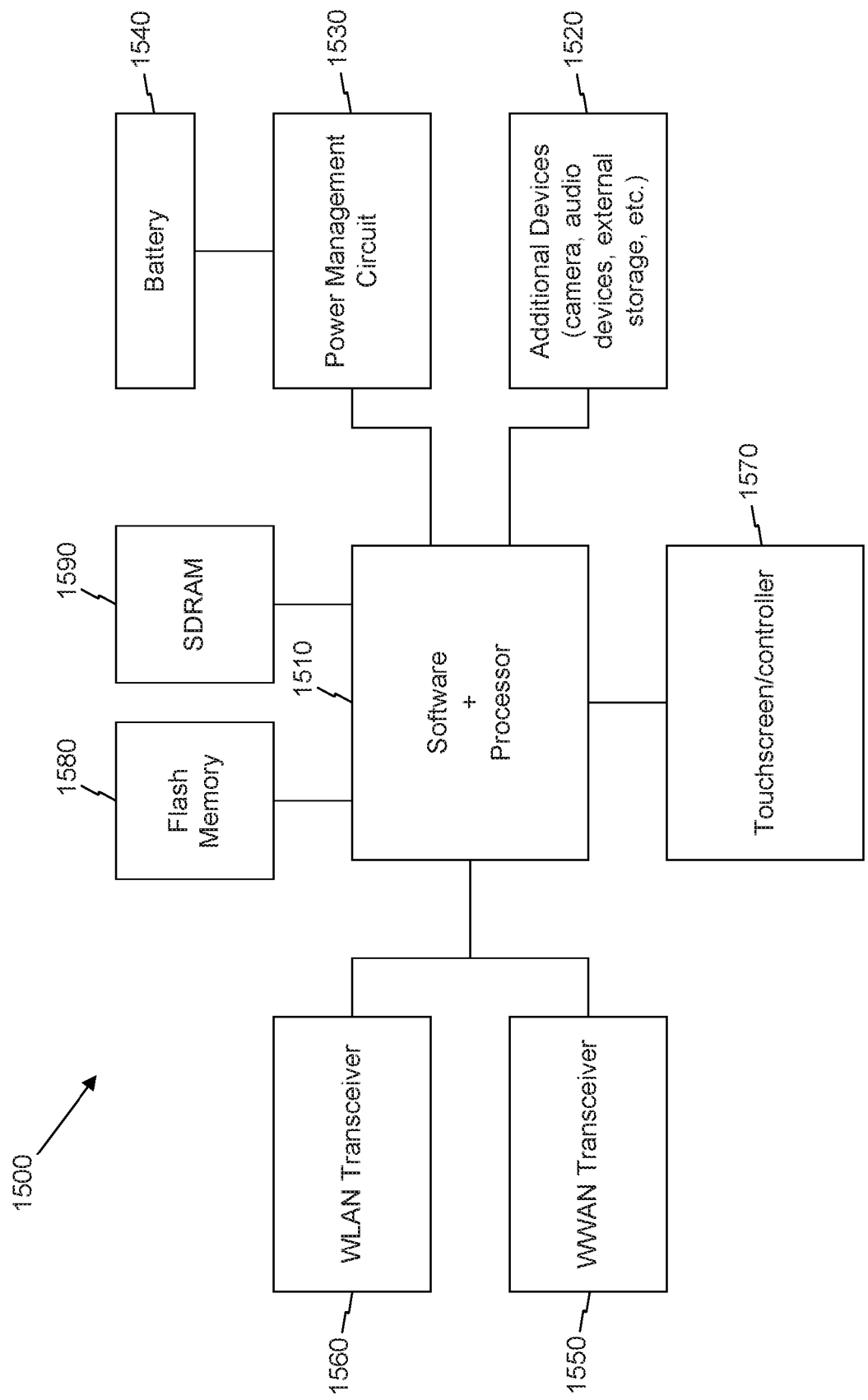
FIG. 15 illustrates an example of computer circuitry that may be used in implementing a system for automated hospital workforce load driven scheduling optimization, consistent with embodiments of the present disclosure.

For example, as illustrated in FIG. 15, with regard to smart phone and/or tablet circuitry 1500, an example includes an ARM based system (system on a chip) design, with software and processor(s) combined in a single chip 1510. Internal busses and the like depend on different vendors, but essentially all the peripheral devices (1520) may attach to a single chip 1510. The tablet circuitry 1500 combines the processor, memory control, and I/O controller hub all into a single chip 1510. Also, ARM based systems 1500 do not typically use SATA or PCI or LPC. Common interfaces for example include SDIO and I2C.

There are power management chip(s) 1530, which manage power as supplied for example via a rechargeable battery 1540, which may be recharged by a connection to a power source (not shown), and in at least one design, a single chip, such as 1510, is used to supply BIOS like functionality and DRAM memory.

ARM based systems 1500 typically include one or more of a WWAN transceiver 1550 and a WLAN transceiver 1560 for connecting to various networks, such as telecommunications networks and wireless base stations. Commonly, an ARM based system 1500 will include a touch screen 1570 for data input and display. ARM based systems 1500 also typically include various memory devices, for example flash memory 1580 and SDRAM 1590. Application programs, e.g., as for example representing functionality of the capacity management module, the staff scheduling module, and/or the scheduling module, may be stored in flash memory 1580 and/or SDRAM 1590 for execution by processor 1510. It will be, however, understood that all such modules or each module and associated code might be distributed between two or more devices as well.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone. Further, while the embodiments described related to patients in a facility, some embodiments may relate to utilization with respect to staff, members of the public, guests, contactors, or equipment.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

What is claimed is:

1. A method, the method comprising:
    receiving current census data for departments of a hospital, wherein the current census data comprises real-time data identifying a number of patients currently admitted within a given of the departments and a current status of the patients;
    generating benchmarking data for the hospital by identifying a performance benchmark for a given of the departments by analyzing real-time data and historical data corresponding to the real-time data, wherein the performance benchmark is based upon at least one performance metric related to efficiency and efficacy of the given of the departments, wherein the benchmarking data identifies a length of time patients spend within each of the departments of the hospital and comprises a comparison of performance metrics across different operational elements of care and throughout a patient itinerary;
    projecting future census data for the departments based upon at least the benchmarking data, wherein the projecting comprises predicting, by analyzing the current census data against the benchmarking data utilizing a trained model, a location of patients within the hospital at a future time, wherein the trained model is iteratively refined upon updates to the benchmarking data;
    displaying, in a dynamic user interface on a facility utilization visualization application, a graphical view of a current utilization of the departments of the hospital determined from the current census data and a projected utilization of the departments determined from the future census data; and
    dynamically updating the dynamic user interface in real-time based upon at least one of receipt of new real-time data, receipt of new historical data, and a new analysis of the real-time and the historical data.

2. The method of claim 1, wherein the projecting future census data comprises projecting a plurality of future census data, each of the plurality of future census data corresponding to a potential level of facility utilization and based upon a probability of occurrence of at least one factor contributing to the potential level of facility utilization.

3. The method of claim 1, wherein the projecting future census data comprises projecting future census data for a time period selected by a user.

4. The method of claim 1, wherein the graphical view further comprises a health score of a given of the departments.

5. The method of claim 4, wherein the health score is computed from the at least one performance metric.

6. The method of claim 5, wherein the health score is further computed by applying the trained model to each of the at least one performance metric to produce at least one weighted metric, wherein the at least one weighted metric is generated by aggregating metric data, normalizing the aggregated data, and applying a weighting factor to different metrics within the normalized aggregated data.

7. The method of claim 4, wherein the health score is computed utilizing a trained model that is created and trained using the at least one performance metric, wherein the trained model predicts projected utilization information, wherein the trained model is iteratively refined upon updates to the at least one performance metric.

8. The method of claim 4, wherein the health score is associated with a period of time, wherein the health score represents an efficiency of the facility at the period of time.

9. The method of claim 1, wherein the projecting comprises utilizing input data from a capacity management system.

10. The method of claim 1, wherein the dynamic user interface comprise graphical representations of transfers of individuals between the departments.

11. An information handling device, the information handling device comprising:
a processor;
a memory device that stores instructions that, when executed by the processor, causes the information handling device to:
receive current census data for departments of a hospital, wherein the current census data comprises real-time data identifying a number of patients currently admitted within a given of the departments and a current status of the patients;
generate benchmarking data for the hospital by identifying a performance benchmark for a given of the departments by analyzing real-time data and historical data corresponding to the real-time data, wherein the performance benchmark is based upon at least one performance metric related to efficiency and efficacy of the given of the departments, wherein the benchmarking data identifies a length of time patients spend within each of the departments of the hospital and comprises a comparison of performance metrics across different operational elements of care and throughout a patient itinerary;
project future census data for the departments based upon at least the benchmarking data, wherein the projecting comprises predicting, by analyzing the current census data against the benchmarking data utilizing a trained model, a location of patients within the hospital at a future time, wherein the trained model is iteratively refined upon updates to the benchmarking data;
display, in a dynamic user interface on a facility utilization visualization application, a graphical view of a current utilization of the departments of the hospital determined from the current census data and a projected utilization of the departments determined from the future census data; and
dynamically update the dynamic user interface in real-time based upon at least one of receipt of new real-time data, receipt of new historical data, and a new analysis of the real-time and the historical data.

12. The information handling device of claim 11, wherein the projecting future census data comprises projecting a plurality of future census data, each of the plurality of future census data corresponding to a potential level of facility utilization and based upon a probability of occurrence of at least one factor contributing to the potential level of facility utilization.

13. The information handling device of claim 11, wherein the projecting future census data comprises projecting future census data for a time period selected by a user.

14. The information handling device of claim 11, wherein the graphical view further comprises a health score of a given of the departments.

15. The information handling device of claim 14, wherein the health score is computed from the at least one performance metric.

16. The information handling device of claim 15, wherein the health score is further computed by applying the trained model to each of the at least one performance metric to produce at least one weighted metric, wherein the at least one weighted metric is generated by aggregating metric data, normalizing the aggregated data, and applying a weighting factor to different metrics within the normalized aggregated data.

17. The information handling device of claim 14, wherein the health score is computed utilizing a trained model that is created and trained using the at least one performance metric, wherein the trained model predicts projected utilization information, wherein the trained model is iteratively refined upon updates to the at least one performance metric.

18. The information handling device of claim 14, wherein the health score is associated with a period of time, wherein the health score represents an efficiency of the facility at the period of time.

19. The information handling device of claim 11, wherein the projecting comprises utilizing input data from a capacity management system.

20. A product, the product comprising:
a non-transitory computer-readable storage device that stores executable code that, when executed by a processor, causes the product to:
receive current census data for departments of a hospital, wherein the current census data comprises real-time data identifying a number of patients currently admitted within a given of the departments and a current status of the patients;
generate benchmarking data for the hospital by identifying a performance benchmark for a given of the departments by analyzing real-time data and historical data corresponding to the real-time data, wherein the performance benchmark is based upon at least one performance metric related to efficiency and efficacy of the given of the departments, wherein the benchmarking data identifies a length of time patients spend within each of the departments of the hospital and comprises a comparison of performance metrics across different operational elements of care and throughout a patient itinerary;
project future census data for the departments based upon at least the benchmarking data, wherein the projecting comprises predicting, by analyzing the current census data against the benchmarking data utilizing a trained model, a location of patients within the hospital at a future time, wherein the trained model is iteratively refined upon updates to the benchmarking data;
display, in a dynamic user interface on a facility utilization visualization application, a graphical view of a current utilization of the departments of the hospital determined from the current census data and a projected utilization of the departments determined from the future census data; and
dynamically update the dynamic user interface in real-time based upon at least one of receipt of new real-time data, receipt of new historical data, and a new analysis of the real-time and the historical data.

\* \* \* \* \*